US010465232B1

(12) United States Patent
Wu et al.

(10) Patent No.: US 10,465,232 B1
(45) Date of Patent: Nov. 5, 2019

(54) METHODS FOR QUANTIFYING EFFICIENCY OF NUCLEIC ACID EXTRACTION AND DETECTION

(71) Applicant: Trace Genomics, Inc., San Francisco, CA (US)

(72) Inventors: Diane Wu, San Francisco, CA (US); Poornima Parameswaran, Millbrae, CA (US); Scott Hickey, San Francisco, CA (US)

(73) Assignee: Trace Genomics, Inc., San Francisco, CA (US)

( * ) Notice: Subject to any disclaimer, the term of this patent is extended or adjusted under 35 U.S.C. 154(b) by 229 days.

(21) Appl. No.: 15/288,674

(22) Filed: Oct. 7, 2016

Related U.S. Application Data

(60) Provisional application No. 62/239,199, filed on Oct. 8, 2015.

(51) Int. Cl.
C12Q 1/68 (2018.01)
C12Q 1/6816 (2018.01)
C12Q 1/6806 (2018.01)

(52) U.S. Cl.
CPC ......... C12Q 1/6816 (2013.01); C12Q 1/6806 (2013.01)

(58) Field of Classification Search
None
See application file for complete search history.

(56) References Cited

U.S. PATENT DOCUMENTS

| 5,604,097 | A | 2/1997 | Brenner | |
|---|---|---|---|---|
| 7,537,897 | B2 | 5/2009 | Brenner et al. | |
| 8,715,967 | B2 | 5/2014 | Casbon et al. | |
| 8,835,358 | B2 | 9/2014 | Fodor et al. | |
| 9,944,973 | B2 * | 4/2018 | Willey | C12Q 1/6851 |
| 2010/0255474 | A1 * | 10/2010 | Russwurm | C12Q 1/689 435/6.13 |
| 2012/0129794 | A1 * | 5/2012 | Dowd | C12Q 1/6809 514/24 |

FOREIGN PATENT DOCUMENTS

| WO | 0006770 | 2/2000 |
|---|---|---|
| WO | 0027521 | 5/2000 |
| WO | 0058507 | 10/2000 |
| WO | 0123610 | 4/2001 |
| WO | 0157248 | 8/2001 |
| WO | 0157249 | 8/2001 |
| WO | 02061127 | 8/2002 |
| WO | 03004690 | 1/2003 |
| WO | 03016565 | 2/2003 |
| WO | 03048387 | 6/2003 |
| WO | 03054142 | 7/2003 |
| WO | 2004018493 | 3/2004 |
| WO | 2004018497 | 3/2004 |
| WO | 2004050915 | 6/2004 |
| WO | 2004069849 | 8/2004 |
| WO | 2004070005 | 8/2004 |
| WO | 2004070007 | 8/2004 |
| WO | 2004076692 | 9/2004 |
| WO | 2005003375 | 1/2005 |
| WO | 2005021786 | 3/2005 |
| WO | 2005047301 | 5/2005 |
| WO | 2005065814 | 7/2005 |
| WO | 2005068089 | 7/2005 |
| WO | 2005068656 | 7/2005 |
| WO | 2005078130 | 8/2005 |
| WO | 2013173394 | 11/2013 |

OTHER PUBLICATIONS

Barquist et al., The TraDIS toolkit: sequencing and analysis for dense transposon mutant libraries, Bioinformatics, vol. 32, No. 7, 2015, pp. 1109-1111.
Bronner et al., Improved Protocols for Illumina Sequencing, Curr. Protoc. Hum Genet, Jul. 2009, pp. 1-46.
Bruenn, A structural and primary sequence comparison of the viral RNA-dependent RNA polymerases, Nucleic Acids Res, vol. 31, No. 7, 2003, pp. 1821-1829.
Clarke et al., Continuous base identification for single-molecule nanopore DNA sequencing, Nat Nanotechnol., vol. 4, Apr. 2009, pp. 265-270.
Devonshire et al., Towards standardisation of cell-free DNA measurement in plasma: controls for extraction efficiency, fragment size bias and quantification, Anal Bioanal Chem., vol. 406, 2014, pp. 6499-6512.
Floyd et al., Nematode-specific PCR primers for the 18S small subunit rRNA gene, Molecular Ecology Notes, vol. 5, 2005, pp. 611-612.
Flusberg et al., Direct detection of DNDNA methylation during single-molecule, real-time sequencing, Nature Methods, vol. 7, No. 6, Jun. 2010, 7 pages.
Fu et al., Molecular indexing enables quantitative targeted RNA sequencing and reveals poor efficiencies in standard library preparations, PNAS, vol. 111, No. 5, Feb. 4, 2014, pp. 1891-1896.
Goryshin et al., Tn5 in Vitro Transposition, Journal of Biological Chemistry, vol. 273, No. 13, 1998, pp. 7367-7374.
Hill et al., Development of a Nucleic Acid Extraction Procedure for Simultaneous Recovery of DNA and RNA from Diverse Microbes in Water, Pathogens, vol. 4, 2015, pp. 335-354.
Isenbarger et al., The Most Conserved Genome Segments for Life Detection on Earth and Other Planets, Orig Life Evol Biosph, vol. 38, 2008, pp. 517-533.

(Continued)

Primary Examiner — Samuel C Woolwine
(74) Attorney, Agent, or Firm — Kilpatrick Townsend & Stockton LLP

(57) ABSTRACT

Methods for quantifying the efficiency of nucleic acid extraction from a sample comprising a mixture of species are provided. In some embodiments, the method comprises adding an initial amount of one or more spike-ins to the sample, extracting nucleic acids from the sample, quantifying the amount of the one or more spike-ins in the extracted nucleic acid sample, and comparing the initial amount of the one or more spike-ins to the quantified amount of the one or more spike-ins.

11 Claims, 6 Drawing Sheets

Specification includes a Sequence Listing.

(56) References Cited

OTHER PUBLICATIONS

Islam et al., Quantitative single-cell RNARNARNA-seq with unique molecular identifiers, Nat Methods, vol. 11, No. 2, Feb. 2014, pp. 163-168.

Kivioja et al., Counting absolute numbers of molecules using unique molecular identifiers, Nat Methods, vol. 9, No. 1, Jan. 2012, 5 pages.

Maiden, Multilocus Sequence Typing of Bacteria, Annu. Rev. Microbiol., vol. 60, 2006, pp. 561-588.

Mardis, Next-Generation DNA Sequencing Methods, Ann. Rev. Genomics Hum. Genet., vol. 9, 2008, pp. 387-402.

McElroy et al., Deep sequencing of evolving pathogen populations: applications, errors, and bioinformatic solutions, Microbial Informatics and Experimentation, vol. 4, No. 1, 2014, pp. 1-14.

Nadkarni et al., Determination of bacterial load by real-time PCR using a broad-range (universal) probe and primers set, Microbiology, vol. 148, 2002, pp. 257-266.

Picelli et al., Tn5 transposase and tagmentation procedures for massively scaled sequencing projects, Genome Res., vol. 24, 2014, pp. 2033-2040.

Purdy, Nucleic Acid Recovery from Complex Environmental Samples, Environmental Nucleic Acid Extraction, Methods in Enzymology, Environmental Microbiology, vol. 397, ., ed, Elsevier Academic Press, 2005, pp. 271-292.

Reznikoff, Tn5 as a model for understanding DNA transposition, Molecular Microbiology, vol. 47, No. 5, 2003, pp. 1199-1206.

Robe et al., Extraction of DNA from soil, European Journal of Soil Biology, vol. 39, 2003, pp. 183-190.

Rohland et al., Cost-effective, high-throughput DNA sequencing libraries for multiplexed target capture, Genome Research, vol. 22, 2012, pp. 939-946.

Schmitt et al., Detection of ultra-rare mutations by next-generation sequencing, PNAS, vol. 109, No. 36, Sep. 4, 2012, pp. 14508-14513.

Van Opijnen et al., Transposon insertion sequencing: a new tool for systems-level analysis of microorganisms, Nature Reviews, Microbiology, vol. 11, Jul. 2013, pp. 435-442.

Bilodeau et al., Development of an Assay for Rapid Detection and Quantification of Verticillium Dahliae in Soil, Phytopathology, vol. 102, No. 3, Mar. 2012, pp. 331-343.

Hadziavdic et al., Characterization of the 18S rRNA Gene for Designing Universal Eukaryote Specific Primers, PLoS One, vol. 9, No. 2, e87624, Feb. 7, 2014, pp. 1-10.

\* cited by examiner

| | | Consensus | 1 'X' PER PRIMER<br>$X_1$ = C,T OR A<br>$X_2$ = C,G OR T<br>$X_3$ = C,A OR T | 2 'X's PER PRIMER<br>$X_4$ = A,C OR G  $X_8$ = C,T OR A<br>$X_5$ = A,G OR T  $X_9$ = A,C OR G<br>$X_6$ = C,G OR T<br>$X_7$ = C,G OR T | 3-10 'X's PER PRIMER |
|---|---|---|---|---|---|
| | | A C G T A A C T G A | A C $X_1$ T A A C T G A<br>A C G T A $X_2$ C T G A<br>A C G T A A C $X_3$ G A<br>... ... ... ... ... ... ... ... ... ... | A C G $X_4$ A A C T G A<br>$X_6$ C G T $X_7$ A C T G A<br>A C $X_8$ T A A $X_5$ T G A<br>A C $X_8$ T A A C $X_9$ G A<br>... ... ... ... ... ... ... ... ... ... | > 2 N's PER PRIMER |
| 70% Consensus NT. | 80% Consensus NT. | 90% Consensus NT. | | | |
| 2.8% | 10.7% | 34.9% | | | |
| 1.2%<br>1.2%<br>1.2%<br>... | 2.7%<br>2.7%<br>2.7%<br>... | 3.9%<br>3.9%<br>3.9%<br>... | | | |
| 0.52%<br>0.52%<br>0.52%<br>... | 0.67%<br>0.67%<br>0.67%<br>... | 0.43%<br>0.43%<br>0.43%<br>... | | | |

FIG. 4

METHODS FOR QUANTIFYING EFFICIENCY OF NUCLEIC ACID EXTRACTION AND DETECTION

CROSS-REFERENCE TO RELATED APPLICATIONS

This application claims priority to U.S. Provisional Application No. 62/239,199, filed Oct. 8, 2015, the entire contents of which are incorporated by reference herein.

SEQUENCE LISTING

The instant application contains a Sequence Listing which has been filed electronically in ASCII format and is hereby incorporated by reference in its entirety. Said ASCII copy, created on Apr. 3, 2019, is named 098583-1025821-000110US_SL.txt and is 1,907 bytes in size.

BACKGROUND OF THE INVENTION

The efficiency and accuracy of methods of identifying and quantifying pathogens in samples, such as environmental samples, can be affected by a number of factors. For example, the efficiency of extracting nucleic acids from a sample may vary depending on the characteristics of the sample or the presence of inhibitors in the sample, or depending upon whether samples are subjected to pretreatment steps prior to extracting the nucleic acids. The detection of nucleic acid sequences in a sample can also be affected by a number of factors, such as nucleotide composition or the concentration of nucleic acids in a sample.

BRIEF SUMMARY OF THE INVENTION

In one aspect, methods for quantifying the efficiency of nucleic acid extraction from a sample comprising a mixture of species are provided. In some embodiments, the method comprises:
  providing the sample comprising the mixture of species;
  adding to the sample an initial amount of one or more spike-ins from one or more species in the mixture, wherein the spike-ins include a known amount of a species;
  extracting nucleic acids from the sample comprising the one or more spike-ins, thereby forming an extracted nucleic acid sample;
  quantifying the one or more spike-ins in the extracted nucleic acid sample to generate a quantified amount of the one or more spike-ins; and
  comparing the initial amount of the one or more spike-ins to the quantified amount of the one or more spike-ins, thereby quantifying the efficiency of the nucleic acid extraction from the sample.

In some embodiments, the quantifying step comprises detecting a nucleic acid sequence in the one or more spike-ins.

In another aspect, methods for quantifying multiple targets in a population of nucleic acid sequences are provided. In some embodiments, the method comprises:
  (a) providing a sample comprising a population of extracted nucleic acid sequences and further comprising an initial known amount of a plurality of spike-ins, wherein the nucleic acid sequences are extracted from a sample comprising multiple species;
  (b) detecting (i) the sequence and amount of a plurality of species targets from the population of extracted nucleic acid sequences and (ii) the amount of the spike-ins that are present in the sample; and
  (c) normalizing the detected amounts of the detected plurality of species targets from step (b) based on the ratio of the initial amounts of the spike-ins and the detected amounts of the spike-ins, thereby quantifying multiple targets in a population of nucleic acid sequences.

In some embodiments, prior to the detecting step, the method further comprises amplifying a plurality of species targets from the population of extracted nucleic acid sequences, wherein the amplifying step comprises:
  adding a plurality of sets of primers to the sample of step (a), wherein each set of primers comprises a forward primer and a reverse primer targeting a nucleotide sequence in the species, and
  performing an amplification reaction.

In some embodiments, prior to the detecting step, the method further comprises enriching the sample for a subset of species targets from the population of extracted nucleic acid sequences, thereby generating an enriched sample. In some embodiments, subsequent to the step of enriching the sample for a subset of species targets, the method further comprises amplifying a plurality of species targets in the enriched sample.

In some embodiments, the multiple species targets that are detected are bacterial, fungal, or viral species and the detecting comprises a sequence in a conserved bacterial, fungal, or viral region. In some embodiments, the detecting comprises detecting a combination of one or more conserved regions of each species target (e.g., one or more conserved bacterial, fungal, or viral regions) and one or more divergent or highly evolving regions of each species target (e.g., one or more highly evolving bacterial, fungal, or viral regions). In some embodiments, the detecting step comprises detecting species targets from two or more different groups (e.g., two or more of bacterial species, phytoplasma species, viral species, viroid species, *rickettsia* species, fungal species, helminth species, protozoan, parasite species, or pest species).

In some embodiments, the normalizing step (c) comprises evaluating the differential amplification of multiple species targets based on nucleotide content by quantifying the amount of each spike-in from the set of synthetic nucleic acid composition ladders and normalizing based on the amount of each spike-in that is detected. In some embodiments, the normalizing step (c) comprises using quality scores from sequencing reads of the plurality of species targets and spike-ins.

In some embodiments, the spike-ins comprise a live or inactivated bacterial species, phytoplasma species, viral species, viroid species, *rickettsia* species, fungal species, helminth species, protozoan, parasite species, and/or pest species. In some embodiments, the spike-ins comprise a synthetic nucleic acid. In some embodiments, the spike-ins comprise synthetic nucleic acid sequences that comprise one or more artificial sequences and/or one or more transposon sequences. In some embodiments, the spike-ins comprise synthetic nucleic acid sequences that comprise an artificial sequence flanked on each end by a transposon sequence. In some embodiments, the spike-ins comprise a synthetic nucleic acid that comprises a sequence corresponding to a species target sequence. In some embodiments, the spike-ins comprise a set of synthetic nucleic acid composition ladders of varying nucleotide content. In some embodiments, the spike-ins comprise a dilution series of a known species (e.g., cell or organism) or a concentration ladder for evaluating differential amplification of multiple species targets based on concentration.

In some embodiments, the sample comprises one or more bacterial species, phytoplasma species, viral species, viroid species, *rickettsia* species, fungal species, helminth species, protozoan, parasite species, and/or pest species. In some embodiments, the sample comprises multiple species. In some embodiments, the one or more bacterial species, phytoplasma species, viral species, viroid species, *rickettsia* species, fungal species, helminth species, protozoan, parasite species, and/or pest species are plant pathogens. In some embodiments, the sample is an environmental sample.

In another aspect, methods for detecting a target in a population of nucleic acid sequences are provided. In some embodiments, the method comprises:
(a) providing a sample comprising a population of extracted nucleic acid sequences, wherein the nucleic acid sequences are extracted from a sample comprising multiple species;
(b) adding to the sample of step (a) a pool of primers, wherein the pool of primers comprises (i) a plurality of primers that comprise a consensus binding sequence, and (ii) a plurality of primers that comprise a sequence with at least one nucleotide variation from the consensus binding sequence, wherein the pool of primers results in variation at one or more nucleotide positions of the consensus binding sequence such that for the varied nucleotide position, at least two different nucleotides selected from adenine, thymine, cytosine, and guanine are represented in the varied nucleotide position in the pool of primers;
(c) amplifying the sample of step (b); and
(d) detecting the presence of the target.

In some embodiments, for the varied nucleotide position, at least one primer in the pool of primers has an adenine nucleotide, at least one primer in the pool of primers has a thymine nucleotide, at least one primer in the pool of primers has a cytosine nucleotide, and at least one primer in the pool of primers has a guanine nucleotide. In some embodiments, for the one or more varied nucleotide positions, the different non-consensus nucleotides are present in approximately equal amounts. In some embodiments, for the one or more varied nucleotide positions, from about 50% to about 95% (e.g., from about 70% to about 95%) of the nucleotides in the primer pool have the consensus nucleotide. In some embodiments, up to about 97% of the primers in the pool have the consensus binding sequence.

In some embodiments, the consensus binding sequence has a length of about 8 to about 50 nucleotides. In some embodiments, the primer pool results in variation in at least about 25% of the nucleotide positions of the consensus binding sequence. In some embodiments, the primer pool results in variation at all of the nucleotide positions of the consensus binding sequence.

In some embodiments, the method comprises detecting a wild-type target sequence comprising a nucleic acid sequence that is entirely complementary to the consensus binding sequence. In some embodiments, the target that is detected is a mutated target sequence comprising a nucleic acid sequence that is not entirely complementary to the consensus binding sequence. In some embodiments, the method comprises detecting (i) a wild-type target sequence that is entirely complementary to the consensus binding sequence, and (ii) a mutated target sequence that is not entirely complementary to the primer consensus binding sequence; and comparing the amount of the mutated target sequence in the sample to the amount of the wild-type target sequence in the sample. In some embodiments, the detecting step (d) comprises nucleotide sequencing the target. In some embodiments, the detecting step (d) comprises deep sequencing.

BRIEF DESCRIPTION OF THE DRAWINGS

FIG. 4. This figure represents the many possible derivatives of the example consensus sequence "ACGTAACTGA" (SEQ ID NO: 1) found in a complex primer pool. Shown are examples for primers with 1 mismatch (1 'X' per primer) SEQ ID NOS 2-4, respectively, in order of appearance, and primers with 2 mismatches (2 'X's per primer) SEQ ID NOS 5-7, respectively, in order of appearance. 'X' can be any non-consensus nucleotides. The column on the right shows the nucleotide possibilities for each X (X1 through X9). The column on the left shows the estimated abundances of each indicated primer sequence, based on 70%, 80%, or 90% consensus nucleotide incorporation at each position along the oligonucleotide. As one example of calculating the abundances of primers, for a primer 10 nucleotides in length with 1 'X' nucleotide and with 9 consensus nucleotides, with 70% consensus incorporation, the abundance is calculated as: $[(0.7^9)*(0.3^1)]*100=1.2\%$. For a primer 10 nucleotides in length with 2 'X' nucleotides and with 8 consensus nucleotides, with 70% consensus incorporation, the abundance is calculated as: $[(0.7^8)*(0.3^2)]*100=0.52\%$.

FIG. 6. Normalization results for quantification of a real (non-synthetic) organism show that spike-in normalization enables linear quantification of real (non-synthetic) organisms. X-axis: Number of spike-in cells of whole organism (*Botrytis cinerea*). Y-axis: Normalized read count for whole organism spike-in. Blue dots depict number of *Botrytis cinerea* sequences captured as a fraction of total reads captured from any fungus. Red dots depict number of *Botrytis cinerea* sequences captured as a fraction of total reads captured from synthetic spike-in.

DEFINITIONS

Figure 1:
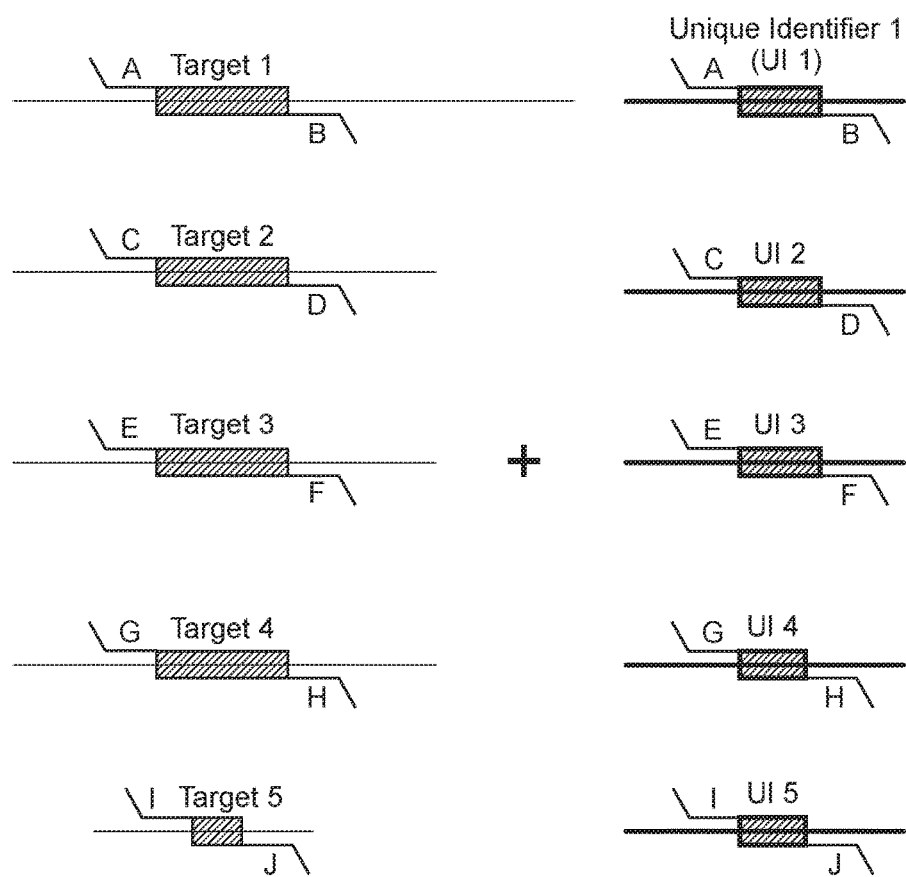
FIG. 1. A normalization method for differential priming of capture primers between multiple targets in a nucleic acid population.
Figure 2:
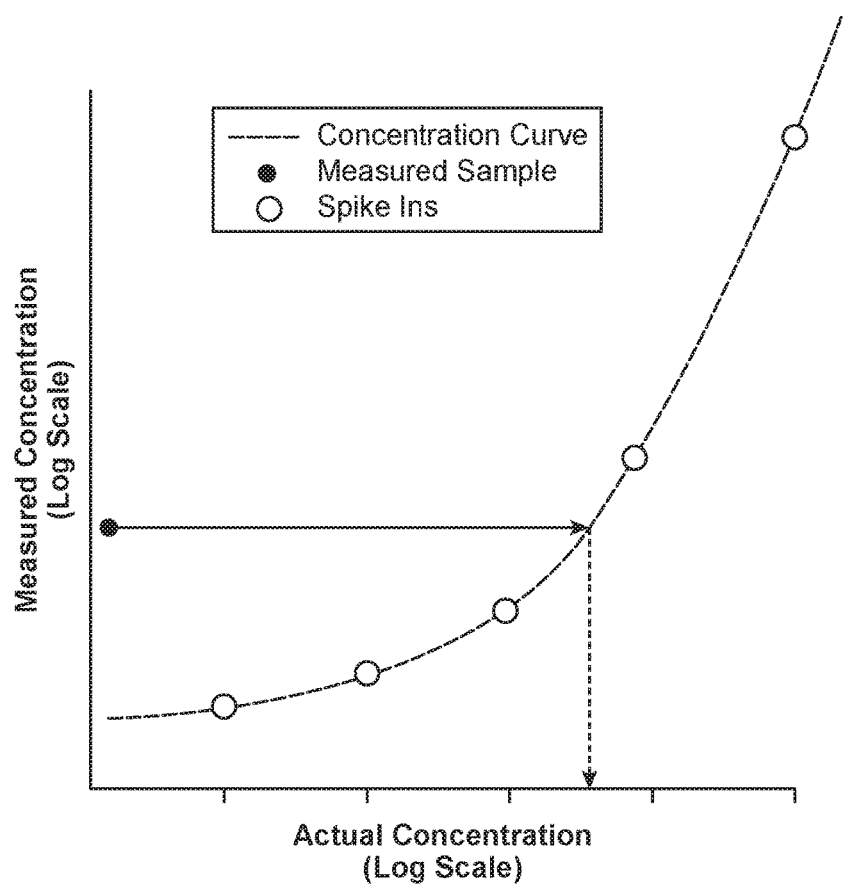
FIG. 2. A normalization method for differential amplification of targets based on concentration.

Unless defined otherwise, technical and scientific terms used herein have the same meaning as commonly understood by a person of ordinary skill in the art. See, e.g., Lackie, DICTIONARY OF CELL AND MOLECULAR BIOLOGY, Elsevier (4$^{th}$ ed. 2007); Sambrook et al., MOLECULAR CLONING, A LABORATORY MANUAL, Cold Spring Harbor Lab Press (Cold Spring Harbor, N.Y. 1989). The term "a" or "an" is intended to mean "one or more." The term "comprise," and variations thereof such as "comprises" and "comprising," when preceding the recitation of a step or an element, are intended to mean that the addition of further steps or elements is optional and not excluded. Any methods, devices and materials similar or equivalent to those described herein can be used in the practice of this invention. The following definitions are provided to facilitate understanding of certain terms used frequently herein and are not meant to limit the scope of the present disclosure.

As used herein, the term "pathogen" refers to a replicating agent that causes a disease. In some embodiments, a pathogen is a "plant pathogen," which as used herein refers to a replicating agent that causes a disease in a plant or a plant part (e.g., plant cell, leaf, flower, seed, or fruit). In some embodiments, a pathogen is a microbial organism (e.g., a bacterium, phytoplasma, virus, viroid, protozoan, *rickettsia*, or fungus). In some embodiments, a pathogen is a bacterium, phytoplasma, virus, viroid, protozoan, *rickettsia*, fungus, helminth, parasite, or pest.

As used herein, the term "spike-in" refers to a molecule(s) (e.g., nucleic acid molecule), cell, or organism (e.g., a microbial organism) that is added to a sample in a known amount and that serves as a control for the sample. In some embodiments, the spike-in is a molecule, cell, or organism that is known not to be present in the sample. In some embodiments, the spike-in is a molecule, cell, or organism that has a detectable tag, barcode, or sequence that facilitates the identification of the spike-in in the sample. In some embodiments, the spike-in is a molecule, cell, or organism that comprises one or more transposon sequences. In some embodiments, a spike-in is a synthetic nucleic acid molecule (e.g., a synthetic DNA or RNA oligonucleotide). In some embodiments, a spike-in is a cell or organism (e.g., a bacterial species, phytoplasma species, viral species, viroid species, *rickettsia* species, fungal species, helminth species, protozoan, parasite species, or pest species).

The terms "nucleic acid" and "polynucleotide" interchangeably refer to deoxyribonucleotide (DNA) or ribonucleotide (RNA) and polymers thereof in either single- or double-stranded form. The term encompasses nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, phosphorothioates, phosphoramidates, methyl phosphonates, chiral-methyl phosphonates, 2-O-methyl ribonucleotides, and peptide nucleic acids (PNAs). In certain applications, the nucleic acid can be a polymer that includes multiple monomer types, e.g., both RNA and DNA subunits.

The term "primer" refers to a polynucleotide sequence that hybridizes to a sequence on a target nucleic acid and serves as a point of initiation of nucleic acid synthesis. Primers can be of a variety of lengths. In some embodiments, a primer is less than 100 nucleotides in length, for example 10-80 nucleotides in length. The length and sequences of primers for use in PCR can be designed based on principles known to those of skill in the art. See, e.g., PCR Protocols: A Guide to Methods and Applications, Innis et al., eds, 1990.

As used herein, the term "target" refers to a molecule or organism whose detection is intended. In some embodiments, a target is a nucleic acid sequence (e.g., an extracted nucleic acid sequence in a population of nucleic acid sequences). In some embodiments, a target is a nucleic acid sequence of a bacterial species, viral species, fungal species, nematode species, parasite species, or pest species.

"Enriching" refers to a step of increasing the relative abundance of one or more components of a mixture as compared to other components of the mixture (e.g., increasing the relative abundance of a target molecule in a population of molecules or increasing the relative abundance of a target nucleic acid sequence in a population of nucleic acid sequences). In some embodiments, the term "enriching" refers to physically separating one or more components of a mixture from other components of the mixture. Enrichment can comprise, for example, physically separating higher molecular weight DNA from lower molecular weight DNA (e.g., by electrophoresis) or by attaching adapters to nucleic acids in a nucleic acid mixture and capturing the nucleic acids attached to the adapters.

"Amplifying" refers to a step of submitting a solution to conditions sufficient to allow for amplification of a polynucleotide if all of the components of the reaction are intact. Components of an amplification reaction include, e.g., primers, a polynucleotide template, polymerase, nucleotides, and the like. The term "amplifying" typically refers to an "exponential" increase in target nucleic acid. However, "amplifying" as used herein can also refer to linear increases in the numbers of a select target sequence of nucleic acid, such as is obtained with cycle sequencing.

The term "artificial sequence" refers to a sequence (e.g., a nucleotide sequence) that is not occurring in nature. Such synthetic sequences are referred to herein as "Artificially Unique Sequences." In some embodiments, an artificial sequence lacks significant sequence identity (e.g., has less than 50%, less than 40%, less than 30%, less than 20%, or less than 10% sequence identity) to any portion of a genome of any organism that is published in a publicly available nucleotide database.

The term "sample" refers to a representative portion of a larger volume. In some embodiments, the sample is an environmental sample (e.g., a soil, dirt, water, air, garbage, or sewage sample). In some embodiments, the sample is a biological sample (e.g., any tissue or bodily fluid obtained from a biological organism, e.g., blood, serum, plasma, platelets, red blood cells, sputum, saliva, tissue (e.g., kidney, lung, liver, heart, brain, nervous tissue, thyroid, eye, skeletal muscle, cartilage, or bone tissue), cells, stool, urine, etc.). In some embodiments, the sample is a food sample (e.g., vegetable, fruit, fish, dairy, grain, or meat sample).

As used herein, the terms "about" or "approximately" mean a range of values including the specified value, which a person of ordinary skill in the art would consider reasonably similar to the specified value. In some embodiments, the term "about" or "approximately" means with a standard deviation using measurements generally acceptable in the art. In some embodiments, the term "about" or "approximately" means a range extending to +10% of the specified value. In some embodiments, the term "about" or "approximately" means the specified value.

DETAILED DESCRIPTION OF THE INVENTION

I. Introduction

In one aspect, the present invention relates to the use of spike-ins for improving the accuracy of nucleic acid detection methods. As described in detail below, in some embodiments, spike-ins are used to correct for biases that can occur in nucleic acid extraction, capture, enrichment, amplification, and/or detection methods, such as biases based on the concentration of nucleic acid molecules in a sample or biases based on nucleic acid composition (e.g., GC content).

In another aspect, the present invention relates to the use of complex primer pools for improving the accuracy of nucleic acid detection methods. As described in detail below, in some embodiments, primer pools that introduce variation at each nucleotide position of a primer sequence are used for detecting targets having genomic diversity in a primer binding site.

II. Spike-Ins

In one aspect, spike-ins are provided that can be used for quantifying or correcting for biases in nucleic acid extraction, capture, enrichment, amplification, and/or detection methods. As used herein, the term "spike-in" refers to a molecule (e.g., nucleic acid molecule), cell, or organism (e.g., a microbial organism) that is added to a sample in a known amount and that serves as a control for the sample. In some embodiments, a spike-in that is added to a sample has a detectable characteristic that is known to be absent from the sample into which the spike-in is added; for example, in some embodiments, a spike-in comprises a detectable tag or barcode (e.g., a random barcode) in a nucleic acid sequence that is not present in the sample into which the spike-in is added.

In some embodiments, a set of spike-ins can be added to a sample, wherein the set provides a range of properties or characteristics that can be used for evaluating efficiency of nucleic acid extraction, amplification, or enrichment for a sample. For example, in some embodiments, a spike-in of a particular molecule, cell, or organism can be added to a sample in a series of known concentrations (e.g., a series of 2, 3, 4, 5, 6, 7, 8, 9, 10 or more concentrations). A series of concentrations of a spike-in can be useful, e.g., for correcting for concentration biases in nucleic acid extraction, capture, enrichment, amplification, and/or detection methods. In some embodiments, a set of spike-ins comprising 2, 3, 4, 5, 6, 7, 8, 9, 10 or more known concentrations of a particular synthetic nucleic acid sequence, bacterial species, viral species, fungal species, nematode species, parasite species, or pest species is added to a sample at the same time. In some embodiments, the set of spike-ins comprises a dilution series of the particular molecule, cell, or organism (e.g., a serial dilution in which the concentration of the particular molecule, cell, or organism is reduced by about 2-fold, 3-fold, 4-fold, 5-fold, 6-fold, 7-fold, 8-fold, 9-fold, 10-fold, 20-fold, or more at each dilution).

Cell or Organism Spike-Ins

In some embodiments, a spike-in is a cell or an organism (e.g., a microbial organism). In some embodiments, the spike-in is a live (e.g., attenuated) or inactivated species of a cell or organism. For example, in some embodiments, a spike-in is a live (e.g., attenuated) or inactivated bacterial species, phytoplasma species, viral species, viroid species, protozoan species, *rickettsia* species, fungal species, helminth species, parasite species, or pest species.

In some embodiments, a spike-in is a live or inactivated bacterial species. In some embodiments, a bacterial species spike-in is a species of Acidovorax, *Aeromonas, Agrobacterium, Alicyclobacillus, Anabaena, Anacystis, Acinetobacter, Acidothermus, Arthrobacter, Azobacter, Bacillus, Bifidobacterium, Brevibacterium, Butyrivibrio, Buchnera, Burkholderia, Candidatus, Campestris, Camplyobacter, Clavibacter, Clostridium, Corynebacterium, Chromatium, Coprococcus, Curtobacterium, Dickeya, Escherichia, Enterococcus, Enterobacter, Erwinia, Fusobacterium, Faecalibacterium, Francisella, Flavobacterium, Geobacillus, Haemophilus, Helicobacter, Klebsiella, Lactobacillus, Lactococcus, Legionella, Ilyobacter, Micrococcus, Microbacterium, Mesorhizobium, Methylobacterium, Methylobacterium, Mycobacterium, Neisseria, Pantoea, Pectobacterium, Phytoplasma, Pseudomonas, Prochlorococcus, Ralstonia, Rhodobacter, Rhodococcus, Rhodopseudomonas, Rhodopseudomonas, Roseburia, Rhodospirillum, Rhodococcus, Scenedesmus, Streptomyces, Streptococcus, Synecoccus, Saccharomonospora, Staphylococcus, Serratia, Salmonella, Shigella, Spiroplasma, Thermoanaerobacterium, Tropheryma, Tularensis, Temecula, Thermosynechococcus, Thermococcus, Ureaplasma, Xanthomonas, Xylella, Yersinia* or *Zymomonas*. In some embodiments, the spike-in is a species of gram-positive bacteria. In some embodiments, the spike-in is a species of gram-negative bacteria. In some embodiments, the spike-in is a species of gram-indeterminate bacteria.

In some embodiments, a spike-in is a live or inactivated phytoplasma species. In some embodiments, a phytoplasma species spike-in is a species of the genus *Candidatus Phytoplasma* (e.g., *Ca. P. japonicum, Ca. P. castaneae, Ca. P. pini, Ca. P. rhamni, Ca. P. allocasuarinae, Ca. P. fragariae, Ca. P. lycopersici, Ca. P. tamaricis, Ca. P. vitis, Ca. P. solani, Ca. P. palmae,* or *Ca. P. oryzae*).

In some embodiments, a spike-in is a live or inactivated viral species. In some embodiments, a viral species spike-in is a species of the viral family Adenoviridae, Arenaviridae, Arteriviridae, Bromoviridae, Bunyaviridae, Caliciviridae, Caulimoviridae, Circoviridae, Closteroviridae, Comoviridae, Coronaviridae, Cystoviridae, Flaviviridae, Geminiviridae, Herpesviridae, Hypoviridae, Iridoviridae, Leviviridae, Myoviridae, Orthomyxoviridae, Paramyxoviridae, Partitiviridae, Parvoviridae, Picornaviridae, Podoviridae, Potyviridae, Poxviridae, Reoviridae, Retroviridae, Rhabdoviridae, Sequiviridae, Siphoviridae, Togaviridae, Tombusviridae, or Totiviridae. In some embodiments, the spike-in is a species of DNA virus (e.g., dsDNA virus or ssDNA virus). In some embodiments, the spike-in is a species of RNA virus (e.g., dsRNA virus or ssRNA virus). In some embodiments, the spike-in is a species of reverse transcribing virus (e.g., retrovirus). In some embodiments, the virus is an enveloped virus. In some embodiments, the virus is a non-enveloped virus.

In some embodiments, a spike-in is a live or inactivated viroid species. In some embodiments, a viroid species spike-in is a species of the viroid family Pospiviroidae (e.g., a species of the genus Pospiviroid, Hostuviroid, Cocadviroid, Apscaviroid, or Coleviroid) or Avsunviroidae (e.g., a species of the genus Avsunviroid, Elaviroid, or Pelamoviroid).

In some embodiments, a spike-in is a live or inactivated *rickettsia* species. In some embodiments, a *rickettsia* species spike-in is a species of *Rickettsia aeschlimannii, R. africae, R. akari, R. asiatica, R. australis, R. canadensis, R. conorii, R. cooleyi, R. felis, R. heilongjiangensis, R. Helvetica, R. honei, R. hulinii, R. japonica, R. massiliae, R. montanensis, R. parkeri, R. peacockii, R. prowazekii, R. rhipicephali, R. rickettsia, R. slovaca, R. tamurae,* or *R. typhi*.

In some embodiments, a spike-in is a live or inactivated fungal species. In some embodiments, a fungal species spike-in is a species of *Absidia, Acremonium, Alternaria, Aphanocladium, Arhrinium, Arthrobotrys, Aspergillus,*

*Aurobasidium, Bjerkandera, Botryosphaeria, Botrytis, Cephalosporium, Cercospora, Ceriporiopsis, Chaeotomium, Cladosporium, Cochliobolus, Colletotrichum, Corynascus, Cryphonectria, Cryptococcus, Coprinus, Coriolus, Curvularia, Cylindrocarpon, Didymella, Diplodia, Drechslera, Elsinoe, Endothis, Engyodontium, Epicoccum, Erisiphae, Eurotium, Eutypa,* Fairy ring fungi, *Fusarium, Gaeumannomyces, Geotrichum, Gibberella, Gliocladium, Gonatobotryum, Histoplasma, Humicola, Hypocrea, Leptosphaeria, Macrophomina, Michrodochium, Microsporum, Monilinia, Mucor, Mycosphaerella, Myrothecium, Myxotrichum, Neurospora, Nigrospora, Paecilomyces, Penicillium, Peronospora, Petriella, Peziza, Phaeoacremonuium, Phaeomoniella, Phoma, Phomopsis, Phytophthora, Phytotrichopsis, Pithomyces, Podospora, Phlebia, Piromyces, Pyricularia, Puccinia, Pythium, Rhizoctonia, Rhizomucor, Rhizopus, Schizophyllum, Sclerotinia, Scopulariopsis, Scytalidium, Septoria, Sporothrix, Sporotrichum, Stachybotrys, Stemphylium, Talaromyces, Torula, Trichoderma, Typhula, Ulocladium, Verticillium, Volvariella,* or *Wallemia.*

In some embodiments, a spike-in is a live or inactivated helminth species. In some embodiments, a helminth species spike-in is a species of *Achlysiella, Anguina, Aphelenchoides, Belonolaimus, Bursaphelenchus, Criconemoides, Ditylenchus, Dolichodorus, Globodera, Gracilacus, Helicotylenchus, Hemicriconemoides, Hemicycliophora, Heterodera, Hirschmanniella, Hoplolaimus, Longidorus, Meloidogyne, Merlinius, Mesocriconema, Naccobus, Paralongidorus, Paratrichodorus, Paratylenchus, Pratylenchus, Quinisulcius, Radopholus, Rotylenchulus, Trichodorus, Tylenchorhynchus, Tylenchulus,* or *Xiphinema.*

In some embodiments, a spike-in is a live or inactivated parasite species. In some embodiments, a parasite species spike-in is a protozoan (e.g., an amoeba, a flagellate, a ciliate, or a sporozoan), a fungal parasite, a nematode, an ectoparasite (e.g., ticks, fleas, lice, and mites), or a plant parasite.

In some embodiments, a spike-in is a live or inactivated pest species. In some embodiments, a pest species spike-in is an insect (e.g., a species of the order Anoplura, Coleoptera, Dermaptera, Diptera, Hemiptera, Hymenoptera, Isoptera, Lepidoptera, Mallophaga, Orthoptera, Psocoptera, Siphonaptera, or Thysanoptera), an arachnid (e.g., a species of the order Acarina), or a nematode (e.g., a species of the genus *Anguina, Belonolaimus, Bursaphelenchus, Criconemoides, Ditylenchus, Globodera, Gracilacus, Helicotylenchus, Hemicycliophora, Heterodera, Hirschmanniella, Hoplolaimus, Longidorus, Meloidogyne, Merlinius, Naccobus, Paratrichodorus, Paratylenchus, Pratylenchus, Quinisulcius, Radopholus, Rotylenchulus, Trichodorus, Tylenchulus,* or *Xiphinema*).

In some embodiments, a spike-in is a mutated cell or organism (e.g., a mutated bacterial species, phytoplasma species, viral species, viroid species, *rickettsia* species, fungal species, helminth species, protozoan, parasite species, or pest species). In some embodiments, the spike-in is a cell or organism that comprises a mutation or heterologous sequence that results in a detectable tag, barcode, or nucleic acid sequence in the genome of the cell or organism. The term "heterologous sequence," as used with reference to a sequence in a cell or organism, refers to a sequence that originates from a foreign species, or if from the same species, is modified from its original form. In some embodiments, the spike-in is a cell or organism that comprises a plasmid comprising a detectable tag, barcode, or nucleic acid sequence. In some embodiments, the detectable tag, barcode, or nucleic acid sequence that is introduced into the spike-in is known to not be present in a sample into which the spike-in will be added.

In some embodiments, a set of cell or organism spike-ins (e.g., a set of 2, 3, 4, 5, 6, 7, 8, 9, 10 or more spike-ins) is provided. For example, in some embodiments, a set of cell or organism spike-ins comprises varying concentrations of a single species (e.g., single bacterial species, phytoplasma species, viral species, viroid species, *rickettsia* species, fungal species, helminth species, protozoan, parasite species, or pest species). In some embodiments, a set of cell or organism spike-ins comprises a plurality of different species (e.g., two or more of bacterial species, phytoplasma species, viral species, viroid species, *rickettsia* species, fungal species, helminth species, protozoan, parasite species, or pest species).

In some embodiments, a plasmid that comprises a detectable tag, barcode, or nucleic acid sequence is transformed into a cell or organism spike-in. In transformation, a polynucleotide (e.g., a polynucleotide comprising a barcode sequence) that is introduced into a cell remains in the genome or on a plasmid or other stably maintained vector in the cell and is capable of being inherited by the progeny thereof. Stable transformation is typically accomplished by transforming the cell with an expression vector comprising a polynucleotide of interest (e.g., a polynucleotide comprising a barcode sequence or other detectable sequence) along with a selectable marker gene (e.g., a gene that confers resistance to an antibiotic). Only those cells which have integrated the polynucleotide sequences of the expression vector into their genome will survive selection with the marker (e.g., antibiotic). These stably transformed cells can then be propagated according to known methods in the art. Methods, reagents, and tools for transforming cells are known in the art. See, for example, in Sambrook et al (2001) *Molecular Cloning: A Laboratory Manual,* 3$^{rd}$ ed., Cold Spring Harbor Laboratory Press, New York. In some embodiments, introduction of a polynucleotide sequence of interest or plasmid comprising the polynucleotide sequence into a cell can be effected by calcium phosphate transfection, DEAE-dextran mediated transfection, PEG-mediated transformation, electroporation, or other common techniques.

In some embodiments, a detectable tag, barcode, or nucleic acid sequence is introduced into a cell or organism (e.g., microbial organism) by integrating the tag, barcode, or nucleic acid sequence into the genome of the cell or organism. Methods of integrating polynucleotide sequences into cells and organisms are known in the art. See, e.g., Itaya et al., *Mol. Gen. Genet.,* 1990, 223:268-272; Heap et al., *Nucleic Acids Res.,* 2012, 40(8):e59; and Fernandes et al., *Biotechnol. Bioeng.,* 2012, 109:2836-2844.

Synthetic Nucleic Acid Spike-Ins

In some embodiments, a spike-in is a synthetic nucleic acid molecule (e.g., DNA or RNA). In some embodiments, the synthetic nucleic acid molecule is an oligonucleotide or polynucleotide sequence of about 10 to about 600 bases in length, about 20 to about 250 bases in length, about 25 to about 100 bases in length, about 100 to about 600 bases in length, or about 150 to about 600 bases in length (e.g., about 10, about 15, about 20, about 25, about 30, about 40, about 50, about 60, about 70, about 80, about 90, about 100, about 150, about 200, about 250, about 300, about 350, about 400, about 450, about 500, about 550, or about 600 bases in length). In some embodiments, the synthetic nucleic acid molecule is an oligonucleotide or polynucleotide sequence of at least about 100 bases, e.g., at least 100, 200, 300, 400, 500, 600, 700, 800, 900, 1000, 1500, 2000, 2500, 3000, 4000, 5000, 6000, 7000, 8000, 9000, 10,000, 15,000, 20,000, 25,000, 30,000, 40,000, 50,000, 60,000, 70,000, 80,000, 90,000, or 100,000 bases or longer. In some embodiments, the synthetic nucleic acid molecule is an oligonucleotide or polynucleotide sequence having a length in the order of kilobases to megabases (e.g., at least about 1 kb, 5 kb, 10 kb, 15 kb, 20 kb, 30 kb, 40 kb, 50 kb, 60 kb, 70 kb, 80 kb, 90 kb, 100 kb, 150 kb, 200 kb, 300 kb, 400 kb, 500 kb, 600 kb, 700 kb, 800 kb, 900 kb, 1 Mb, 1.5 Mb, 2 Mb, or longer).

In some embodiments, the spike-in is a single-stranded nucleic acid molecule (e.g., single-stranded DNA or single-stranded RNA). In some embodiments, the spike-in is a double-stranded nucleic acid molecule (e.g., double-stranded DNA or double-stranded RNA).

In some embodiments, the nucleotide composition of the synthetic nucleic acid spike-in can be varied to have a desired level of content of one or more nucleotides (adenine, thymine, cytosine, and/or guanine content). For example, in some embodiments, a synthetic nucleic acid spike-in can have a high GC (guanine+cytosine) content (e.g., at least 60%, at least 65%, at least 70%, at least 75%, at least 80%, at least 85%, at least 90%, at least 95%, or more). In some embodiments, a synthetic nucleic acid spike-in can have a high AT (adenine+thymine) content (e.g., at least 60%, at least 65%, at least 70%, at least 75%, at least 80%, at least 85%, at least 90%, at least 95%, or more). In some embodiments, a synthetic nucleic acid spike-in can have a high content of a single nucleotide (e.g., for one of adenine, thymine, cytosine, or guanine, at least 50%, at least 55%, at least 60%, at least 65%, at least 70%, at least 75%, at least 80%, at least 85%, at least 90%, at least 95%, or more of the total content of the nucleotide sequence). In some embodiments, a synthetic nucleic acid spike-in can comprise a variable sequence region of varying adenine, thymine, cytosine, and/or guanine content (e.g., a variable sequence region having high GC content, high AT content, or high content of a single nucleotide) flanked by a forward primer binding sequence and a reverse primer binding sequence.

In some embodiments, a synthetic nucleic acid spike-in comprises a sequence that forms a self-hairpin structure. For example, in some embodiments, a synthetic nucleic acid spike-in comprises a 5' region and a 3' region that can anneal to each other to form a hairpin structure.

In some embodiments, a set of synthetic nucleic acid spike-ins is provided. In some embodiments, the spike-ins comprise a set of synthetic nucleic acid composition ladders of varying nucleotide (adenine, thymine, cytosine, and/or guanine) content. In some embodiments, the spike-ins comprise a set of synthetic nucleic acid composition ladders of varying levels of GC (cytosine and guanine) content. In some embodiments, the spike-ins comprise a set of varying concentrations of a synthetic nucleic acid sequence. In some embodiments, the spike-ins comprise a set of synthetic nucleic acid spike-ins that comprise a sequence that forms a self-hairpin structure (e.g., a set of spike-ins that form hairpin structures of varying strength). In some embodiments, the spike-ins comprise a set of synthetic nucleic acid spike-ins of varying lengths to form a size ladder.

In some embodiments, the synthetic nucleic acid spike-in comprises a detectable tag, barcode, or nucleic acid sequence as discussed below.

Detectable Tags and Sequences

In some embodiments, a spike-in (e.g., a synthetic nucleic acid spike-in or a mutated cell or organism spike-in) comprises a detectable tag, label, barcode, or nucleic acid sequence that facilitates detection of the spike-in in a sample or after one or more steps of processing a sample (e.g., after performing DNA extraction or after an amplification step).

In some embodiments, a spike-in comprises a random nucleotide sequence (barcode) that is unique to that particular spike-in and which allows for the spike-in to be identified. In some embodiments, the barcode comprises a portion of sequence (barcode portion) that is specific to one spike-in. In some embodiments, the barcode portion that is specific to one spike-in has a length of 3, 4, 5, 6, 7, 8, 9, 10, 11, 12, 13, 14, 15, 16, 17, 18, 19, 20, 25, 30, 35, 40, 45, 50, 55, 60, 65, 70, 75, 80 or more bases. In some embodiments, the barcode portion is the length of the spike-in sequence minus the number of primer binding bases. The length of the barcode portion may be selected to provide a desired number of unique barcodes. In some embodiments, a barcode sequence further comprises one or more additional portions that may provide functionality for sample processing steps (e.g., for amplification or sequencing). For example, in some embodiments, the barcode sequence may comprise a universal sequence (a nucleic acid sequence common to all barcodes), or the barcode sequence may comprise a primer sequence for use in an amplification step or a sequencing step. In some embodiments, the total length of the barcode (barcode portion plus any desired additional portions) is about 3, 4, 5, 6, 7, 8, 9, 10, 11, 12, 13, 14, 15, 16, 17, 18, 19, 20, 21, 22, 23, 24, 25, 30, 35, 40, 45, 50, 55, 60, 65, 70, 75, 80 or more bases. In some embodiments, the barcode has a length of about 4 to about 30 bases, of about 6 to about 20 bases, or of about 5 to about 10 bases. In some embodiments, a barcode comprises a "unique molecular identifier" (UMI) sequence (e.g., a sequence used to label a population of nucleic acid molecules such that each molecule in the population has a different identifier associated with it). Barcode and UMI technologies, and methods of labeling nucleic acid molecules with a barcode or UMI sequence, are known in the art. see, e.g., Fu et al. (2014), *PNAS* 111:1891-1896; Islam et al. (2014) *Nat Methods* 11:163-168; Kivioja et al., *Nat Methods* 9:72-74 (2012); U.S. Pat. Nos. 5,604,097; 7,537,897; 8,715,967; 8,835,358; and WO 2013/173394.

In some embodiments, a spike-in comprises one or more synthetic sequences that are designed to be non-natural, not occurring in nature, and orthogonal to all known DNA sequences within publicly available nucleotide databases. Such synthetic sequences are referred to herein as "Artificially Unique Sequences." In some embodiments, an Artificially Unique Sequence, or AUS, is generated using a computational algorithm that selects sequences based on lack of significant sequence identity (e.g., less than 50%, less than 40%, less than 30%, less than 20%, or less than 10% sequence identity) to any portion of the genome of any existing organism ever sequenced and placed into any public repository. In some embodiments, an AUS that is used in a spike-in has been selected for one or more functionality variables, such as length, GC content, secondary structure, ability to clone and replicate in a bacterial host without toxicity, ability to amplify by PCR, and ability to sequence according to standard techniques. In some embodiments, an AUS that is used in a spike-in has a length of about 50 bases to about 100,000 bases, e.g., about 50-100,000, 50-50,000, 50-10,000, 50-5,000, 50-1000, 100-5,000, 100-1000, 200-5,000, or 200-1000 bp, e.g., about 50, 100, 150, 200, 250, 300, 400, 500, 600, 700, 800, 900, 1000, 1500, 2000, 2500, 3000, 4000, 5000, 6000, 7000, 8000, 9000, 10,000, 15,000, 20,000, 25,000, 30,000, 40,000, 50,000, 60,000, 70,000, 80,000, 90,000, or 100,000 bases. In some embodiments, an AUS has a minimum length of at least about 50 bp, 100 bp, 150 bp, 200 bp, or 250 bp. In some embodiments, a spike-in comprises about 1, 2, 3, 4, 5, 6, 7, 8, 9, 10, 15, 20, 25, 30, 35, 40, 50, 60, 70, 80, 90, 100 AUSs or more. In some embodiments, wherein a spike-in comprises more than one AUS, each AUS sequence is distinct from each other (i.e., the AUS sequences are not identical to each other). In some embodiments, wherein a spike-in comprises more than one AUS, at least some of the AUS sequences are the same. In some embodiments, wherein a spike-in comprises more than one AUS, each AUS sequence is the same.

In some embodiments, a spike-in comprises one or more transposon sequences. In some embodiments, the use of one or more transposon sequences enables the spike-in to be captured in the preparation of sequencing libraries via a transposon sequencing method. Transposon sequences and sequencing methods comprising the use of transposons are known in the art. See, e.g., Goryshin et al., *Journal of Biological Chemistry*, 1998, 273:7367-7374; Reznikoff, Molecular Microbiology, 2003, 47:1199-1206; van Opijnen et al., *Nature Reviews Microbiology*, 2013, 11:435-442; Picelli et al., *Genome Res*, 2014, 24:2033-2040; and Barquist et al., *Bioinformatics*, 2015, 32:1109-1111. In some embodiments, a transposon sequence comprises a sequence or structure as described in Goryshin et al., *Journal of Biological Chemistry*, 1998, 273:7367-7374, or Picelli et al., *Genome Res*, 2014, 24:2033-2040, incorporated by reference herein. In some embodiments, a transposon sequence that is used in a spike-in has a length of about 50 bases to about 100,000 bases, e.g., about 50-100,000, 50-50,000, 50-10,000, 50-5,000, 50-1000, 100-5,000, 100-1000, 200-5,000, or 200-1000 bases. In some embodiments, a spike-in comprises about 1, 2, 3, 4, 5, 6, 7, 8, 9, 10, 15, 20, 25, 30, 35, 40, 50, 60, 70, 80, 90, 100 transposon sequences or more.

In some embodiments, a spike-in comprises an AUS flanked on each side by a transposon sequence. In some embodiments, a spike-in comprises multiple AUSs and transposon sequences, wherein the transposon sequences are spaced between the AUSs. In some embodiments, a spike-in comprises a nucleotide sequence comprising a plurality of AUSs and transposon sequences, wherein the nucleotide sequence has a length in the order of kilobases to megabases (e.g., at least about 1 kb, 5 kb, 10 kb, 15 kb, 20 kb, 30 kb, 40 kb, 50 kb, 60 kb, 70 kb, 80 kb, 90 kb, 100 kb, 150 kb, 200 kb, 300 kb, 400 kb, 500 kb, 600 kb, 700 kb, 800 kb, 900 kb, 1 Mb, 1.5 Mb, 2 Mb, or more).

In some embodiments, a spike-in comprises an optically detectable agent such as a fluorescent agent, phosphorescent agent, chemiluminescent agent, etc. Numerous agents (e.g., dyes, probes, or indicators) are known in the art. (See, e.g., Invitrogen, *The Handbook—A Guide to Fluorescent Probes and Labeling Technologies*, Tenth Edition (2005)). Fluorescent agents can include a variety of organic and/or inorganic small molecules or a variety of fluorescent proteins and derivatives thereof. In some embodiments, the agent is a fluorophore. A vast array of fluorophores are reported in the literature and thus known to those skilled in the art, and many are readily available from commercial suppliers to the biotechnology industry. Literature sources for fluorophores include Cardullo et al., *Proc. Natl. Acad. Sci. USA* 85: 8790-8794 (1988); Dexter, D. L., *J. of Chemical Physics* 21: 836-850 (1953); Hochstrasser et al., *Biophysical Chemistry* 45: 133-141 (1992); Selvin, P., *Methods in Enzymology* 246: 300-334 (1995); Steinberg, I. *Ann. Rev. Biochem.*, 40: 83-114 (1971); Stryer, L. *Ann. Rev. Biochem.*, 47: 819-846 (1978); Wang et al., *Tetrahedron Letters* 31: 6493-6496 (1990); Wang et al., *Anal. Chem.* 67: 1197-1203 (1995). Non-limiting examples of fluorophores include cyanines, fluoresceins (e.g., 5'-carboxyfluorescein (FAM), Oregon Green, and Alexa 488), rhodamines (e.g., N,N,N',N'-tetramethyl-6-carboxyrhodamine (TAMRA), tetramethyl rhodamine, and tetramethyl rhodamine isothiocyanate (TRITC)), eosin, coumarins, pyrenes, tetrapyrroles, arylmethines, oxazines, polymer dots, and quantum dots.

In some embodiments, the agent is an intercalating agent. Intercalating agents produce a signal when intercalated in double stranded nucleic acids. Exemplary agents include SYBR GREEN™, SYBR GOLD™, and EVAGREEN™.

In some embodiments, the agent is a radioisotope. Radioisotopes include radionuclides that emit gamma rays, positrons, beta and alpha particles, and X-rays. Suitable radionuclides include but are not limited to $^{225}$Ac, $^{72}$As, $^{211}$At, $^{11}$B, $^{128}$Ba, $^{212}$Bi, $^{75}$Br, $^{77}$Br, $^{14}$C, $^{109}$Cd, $^{62}$Cu, $^{64}$Cu, $^{67}$Cu, $^{18}$F, $^{67}$Ga, $^{68}$Ga, $^{3}$H, $^{166}$Ho, $^{123}$I, $^{124}$I, $^{125}$I, $^{130}$I, $^{131}$I, $^{111}$In, $^{177}$Lu, $^{13}$N, $^{15}$O, $^{32}$P, $^{33}$P, $^{212}$Pb, $^{103}$Pd, $^{186}$Re, $^{188}$Re, $^{47}$Sc, $^{153}$Sm, $^{89}$Sr, $^{99m}$Tc, $^{88}$Y and $^{90}$Y.

A detectable agent can be detected using any of a variety of detector devices. Exemplary detection methods include radioactive detection, optical absorbance detection (e.g., fluorescence or chemiluminescence), or mass spectral detection. As a non-limiting example, a fluorescent agent can be detected using a detector device equipped with a module to generate excitation light that can be absorbed by a fluorescer, as well as a module to detect light emitted by the fluorescer.

III. Samples

A sample for use in the methods described herein can in some embodiments comprise a mixture of multiple species. In some embodiments, a sample for use in the methods described herein includes material that is known or suspected of containing one or more pathogens (e.g., one or more species of bacteria, phytoplasma, viruses, viroids, *rickettsia*, fungi, protozoans, helminths, parasites, or pests). In some embodiments, the sample comprises one or more bacterial species, phytoplasma species, viral species, viroid species, *rickettsia* species, fungal species, protozoan species, helminth species, parasite species, and/or pest species that are plant pathogens.

In some embodiments, the sample is an environmental sample (e.g., a soil, dirt, water, air, garbage, or sewage sample). In some embodiments, the sample is a biological sample. In some embodiments, the sample is a food sample (e.g., vegetable, fruit, fish, dairy, grain, or meat sample). In some embodiments, the sample is a sample that comprises plants and/or plant parts.

In some embodiments, the sample comprises a mixture of two or more sample types (e.g., two or more environmental samples, biological samples, food samples, and/or samples comprising plants and/or plant parts). In some embodiments, the sample comprises a mixture of two or more sample types wherein one or more of the sample types is tagged or barcoded prior to mixing the sample types. In some embodiments, one or more of the sample types is not tagged or barcoded prior to mixing the sample types.

In some embodiments, the sample comprises one or more bacterial species. In some embodiments, the bacterial species is a species of *Acidovorax, Aeromonas, Agrobacterium, Alicyclobacillus, Anabaena, Anacystis, Acinetobacter, Acidothermus, Arthrobacter, Azobacter, Bacillus, Bifidobacterium, Brevibacterium, Buchnera, Burkholderia, Butyrivibrio, Candidatus, Campestris, Camplyobacter, Clostridium, Clavibacter, Corynebacterium, Chromatium, Coprococcus, Curtobacterium, Dickeya, Escherichia, Enterococcus, Enterobacter, Erwinia, Fusobacterium, Faecalibacterium,*

*Francisella, Flavobacterium, Geobacillus, Haemophilus, Helicobacter, Klebsiella, Lactobacillus, Lactococcus, Legionella, Ilyobacter, Micrococcus, Microbacterium, Mesorhizobium, Methylobacterium, Methylobacterium, Mycobacterium, Neisseria, Pantoea, Pectobacterium, Phytoplasma, Pseudomonas, Prochlorococcus, Ralstonia, Rhodobacter, Rhodococcus, Rhodopseudomonas, Rhodopseudomonas, Roseburia, Rhodospirillum, Rhodococcus, Scenedesmus, Streptomyces, Streptococcus, Synecoccus, Saccharomonospora, Staphylococcus, Serratia, Salmonella, Shigella, Spiroplasma, Thermoanaerobacterium, Tropheryma, Tularensis, Temecula, Thermosynechococcus, Thermococcus, Ureaplasma, Xanthomonas, Xylella, Yersinia* or *Zymomonas* In some embodiments, the bacterial species is a species of *Clavibacter, Xanthomonas, Curtobacterium, Pseudomonas, Acidovorax, Ralstonia, Phytoplasma, Agrobacterium, Xylella, Candidatus*, or *Pectobacterium*.

In some embodiments, the sample comprises one or more viral species. In some embodiments, the viral species is a species of the viral family Adenoviridae, Arenaviridae, Arteriviridae, Bromoviridae, Bunyaviridae, Caliciviridae, Caulimoviridae, Circoviridae, Closteroviridae, Comoviridae, Coronaviridae, Cystoviridae, Flaviviridae, Geminiviridae, Herpesviridae, Hypoviridae, Iridoviridae, Leviviridae, Myoviridae, Orthomyxoviridae, Paramyxoviridae, Partitiviridae, Parvoviridae, Picornaviridae, Podoviridae, Potyviridae, Poxviridae, Reoviridae, Retroviridae, Rhabdoviridae, Sequiviridae, Siphoviridae, Togaviridae, Tombusviridae, or Totiviridae. In some embodiments, the viral species is a species of DNA virus (e.g., dsDNA virus or ssDNA virus). In some embodiments, the viral species is a species of RNA virus (e.g., dsRNA virus or ssRNA virus). In some embodiments, the viral species is a species of reverse transcribing virus (e.g., retrovirus).

In some embodiments, the sample comprises one or more viroid species. In some embodiments, the viroid species is a species of the viroid family Pospiviroidae (e.g., a species of the genus Pospiviroid, Hostuviroid, Cocadviroid, Apscaviroid, or Coleviroid) or Avsunviroidae (e.g., a species of the genus Avsunviroid, Elaviroid, or Pelamoviroid).

In some embodiments, the sample comprises one or more *rickettsia* species. In some embodiments, the *rickettsia* species is a species of *Rickettsia aeschlimannii, R. africae, R. akari, R. asiatica, R. australis, R. canadensis, R. conorii, R. cooleyi, R. felis, R. heilongjiangensis, R. Helvetica, R. honei, R. hulinii, R. japonica, R. massiliae, R. montanensis, R. parkeri, R. peacockii, R. prowazekii, R. rhipicephali, R. rickettsia, R. slovaca, R. tamurae*, or *R. typhi*.

In some embodiments, the sample comprises one or more fungal species. In some embodiments, the fungal species is a species of *Absidia, Acremonium, Alternaria, Aphanocladium, Arhrinium, Arthrobotrys, Aspergillus, Aurobasidium, Bjerkandera, Botryosphaeria, Botrytis, Cephalosporium, Cercospora, Ceriporiopsis, Chaeotomium, Cladosporium, Cochliobolus, Colletotrichum, Corynascus, Cryphonectria, Cryptococcus, Coprinus, Coriolus, Curvularia, Cylindrocarpon, Didymella, Diplodia, Drechslera, Elsinoe, Endothis, Engyodontium, Epicoccum, Erisiphae, Eurotium, Eutypa*, Fairy ring fungi, *Fusarium, Gaeumannomyces, Geotrichum, Gibberella, Gliocladium, Gonatobotryum, Histoplasma, Humicola, Hypocrea, Leptosphaeria, Macrophomina, Michrodochium, Microsporum, Monilinia, Mucor, Mycosphaerella, Myrothecium, Myxotrichum, Neurospora, Nigrospora, Paecilomyces, Penicillium, Peronospora, Petriella, Peziza, Phaeoacremonuium, Phaeomoniella, Phoma, Phomopsis, Phytophthora, Phytotrichopsis, Pithomyces, Podospora, Phlebia, Piromyces, Pyricularia, Puccinia, Pythium, Rhizoctonia, Rhizomucor, Rhizopus, Schizophyllum, Sclerotinia, Scopulariopsis, Scytalidium, Septoria, Sporothrix, Sporotrichum, Stachybotrys, Stemphylium, Talaromyces, Torula, Trichoderma, Typhula, Ulocladium, Verticillium, Volvariella*, or *Wallemia*. In some embodiments, the fungal species is a species of *Phoma, Alternaria, Mycosphaerella, Colletotrichum, Cercospora, Peronospora, Septoria, Didymella, Verticillium, Fusarium, Pyricularia, Cladosporium, Stemphylium, Phytophthora, Botrytis, Cylindrocarpon, Phomopsis, Monilinia, Phaeoacremonuium, Phaeomoniella, Cylindrocarpon, Eutypa, Botryosphaeria, Rhizoctonia, Pythium, Sclerotinia, Michrodochium, Gaeumannomyces, Leptosphaeria, Typhula, Drechslera, Erisiphae, Pyricularia, Puccinia*, Fairy ring fungi, *Gliocladium, Phytotrichopsis, Elsinoe*, or *Macrophomina*.

In some embodiments, the sample comprises one or more helminth species. In some embodiments, the helminth species is a species of *Achlysiella, Anguina, Aphelenchoides, Belonolaimus, Bursaphelenchus, Criconemoides, Ditylenchus, Dolichodorus, Globodera, Gracilacus, Helicotylenchus, Hemicriconemoides, Hemicycliophora, Heterodera, Hirschmanniella, Hoplolaimus, Longidorus, Meloidogyne, Merlinius, Mesocriconema, Naccobus, Paralongidorus, Paratrichodorus, Paratylenchus, Pratylenchus, Quinisulcius, Radopholus, Rotylenchulus, Trichodorus, Tylenchorhynchus, Tylenchulus*, or *Xiphinema*.

In some embodiments, the sample comprises one or more parasite species. In some embodiments, the parasite is a protozoan (e.g., an amoeba, a flagellate, a ciliate, or a sporozoan), a fungal parasite, a nematode, an ectoparasite (e.g., ticks, fleas, lice, and mites), or a plant parasite.

In some embodiments, the sample comprises one or more pest species. In some embodiments, the pest species is a is an insect (e.g., a species of the order Anoplura, Coleoptera, Dermaptera, Diptera, Hemiptera, Hymenoptera, Isoptera, Lepidoptera, Mallophaga, Orthoptera, Psocoptera, Siphonaptera, or Thysanoptera), an arachnid (e.g., a species of the order Acarina), or a nematode (e.g., a species of the genus *Anguina, Belonolaimus, Bursaphelenchus, Criconemoides, Ditylenchus, Globodera, Gracilacus, Helicotylenchus, Hemicycliophora, Heterodera, Hirschmanniella, Hoplolaimus, Longidorus, Meloidogyne, Merlinius, Naccobus, Paratrichodorus, Paratylenchus, Pratylenchus, Quinisulcius, Radopholus, Rotylenchulus, Trichodorus, Tylenchulus*, or *Xiphinema*).

In some embodiments, a sample comprises a mixture of multiple species (e.g., 2, 3, 4, 5, 6, 7, 8, 9, 10, 15, 20, 25, 30, 40, 50, 100, 150, 200, 300, 400, 500, 600, 700, 800, 900, 1000 or more species) from the same class or category, or from two or more classes or categories, as described herein (e.g., species from one of more of the categories of bacteria, viruses, fungi, nematodes, parasites, and/or pests).

Samples can be collected by methods known in the art. For example, samples such as environmental samples can be collected by swabs, wipes, vacuuming, water sampling, or air sampling. In some embodiments, a sample is collected into a container.

In some embodiments, a sample is not subjected to processing prior to being used in the methods of the present invention. In some embodiments, a sample is subjected to one or more processing steps before being used in the methods of the present invention (e.g., the methods as described in Sections IV through VI below). For example, in some embodiments, a sample is liquefied, fragmented, homogenized, pulverized, crushed, chopped, diluted, concentrated, filtered, pulsified, sonicated, or a combination thereof. Exemplary methods are described in Ausubel et al.,

*Current Protocols in Molecular Biology* (1994); Sambrook and Russell, "Fragmentation of DNA by sonication," *Cold Spring Harbor Protocols* (2006); and Burden, "Guide to the Homogenization of Biological Samples," *Random Primers* (2008), pages 1-14.

IV. Methods of Quantifying Nucleic Acid Extraction Efficiency

In another aspect, methods for quantifying the efficiency of nucleic acid extraction from a sample using spike-ins are provided. The inclusion of one or more spike-ins in a sample prior to performing a nucleic acid extraction step can improve accuracy of quantification or correct for biases that occur in the nucleic acid extraction process. For example, in some embodiments, spike-ins can be selected that have a particular property, such as pH, cell wall composition, or another cellular composition, that can affect extraction efficiency. In some embodiments, multiple spike-ins can be selected that exhibit a range of a particular property (e.g., spike-ins having different pHs, different cell wall compositions, or other differences in composition).

In some embodiments, the method comprises:
  providing a sample comprising the mixture of species;
  adding to the sample an initial amount of one or more spike-ins from one or more species in the mixture, wherein the spike-ins include a known amount of a species;
  extracting nucleic acids from the sample comprising the one or more spike-ins, thereby forming an extracted nucleic acid sample;
  quantifying the one or more spike-ins in the extracted nucleic acid sample to generate a quantified amount of the one or more spike-ins; and
  comparing the initial amount of the one or more spike-ins to the quantified amount of the one or more spike-ins, thereby quantifying the efficiency of the nucleic acid extraction from the sample.

Spike-Ins

In some embodiments, the spike-in is a cell or organism as discussed in Section II above (e.g., a live (e.g., attenuated) or inactivated species of a cell or organism, or a mutated cell or organism that is a bacterial species, phytoplasma species, viral species, viroid species, *rickettsia* species, fungal species, helminth species, protozoan, parasite species, or pest species). In some embodiments, the spike-in is a synthetic nucleic acid (e.g., synthetic DNA or RNA sequence) as discussed in Section II above.

The initial amount of the spike-in that is added to the sample is a known amount. For spike-ins that are cells or organisms, the "known amount" of the spike-in is determined by reference to cell count. In some embodiments, the initial amount of a spike-in that is added to the sample is about 1, about 5, about 10, about 50, about 100, about 200, about 300, about 400, about 500, about 600, about 700, about 800, about 900, about 1000, about 1500, about 2000, about 3000, about 4000, about 5000, about 10,000 ($10^4$), about $10^5$, about $10^6$, about $10^7$, about $10^8$, about $10^9$, or about $10^{10}$ cells. In some embodiments, the amount of a spike-in is measured in cells per unit volume (e.g., cells per ml, cells per µl, or cells per nl). In some embodiments, the initial amount of a spike-in that is added to the sample is from about 1 cell/ml to about $10^{10}$ cells/ml (e.g., about $10^2$ cells/ml to about $10^{10}$ cell/ml, about $10^3$ cells/ml to about $10^9$ cells/ml, or about $10^4$ cells/ml to about $10^8$ cells/ml). In some embodiments, the initial amount of a spike-in that is added to the sample is from about 1 cell/µl to about $10^{10}$ cells/µl (e.g., about $10^2$ cells/µl to about $10^{10}$ cell/µl, about $10^3$ cells/µl to about $10^9$ cells/µl, or about $10^4$ cells/µl to about $10^8$ cells/µl). Cell count and cells per unit volume can be determined by any of a number of methods. For example, cell count can be determined using a counting chamber (e.g., hemocytometer) viewed under microscopy; by flow cytometry; by plating a sample followed by colony forming unit (CFU) counting; by measuring the light absorption of a culture comprising the spike-in with a spectrophotometer; by weighing cell, microbial, or tissue biomass and correlating the measurements to a standard to determine the number of cells; or by measuring the amount of nucleic acid (e.g., by real-time PCR or digital PCR) and correlating the measurements to a standard. See, e.g., Nadkarni et al., *Microbiology*, 2002, 148:257-266. In some embodiments, an initial amount of a cell or organism spike-in is determined by measuring cell count or cells per unit volume, and a subsequent measurement of the amount of the cell or organism spike-in is determined by measuring the molecular count of the spike-in in the extracted nucleic acid sample.

For spike-ins that are synthetic nucleic acids, the "known amount" of the spike-in can be, for example, determined by reference to molar quantity. In some embodiments, the initial amount of a spike-in that is added to the sample is about 0.001 pM to about 1 mM, about 0.01 pM to about 1 mM, about 0.1 pM to about 1 mM, about 1 pM to about 1 mM, about 1 nM to about 1 mM, about 100 nM to about 1 mM, 1 nM to about 100 µM, about 1 nM to about 1000 nM, or about 500 nM to about 50 µM (e.g., about 1 nM, about 10 nM, about 50 nM, about 100 nM, about 200 nM, about 300 nM, about 400 nM, about 500 nM, about 600 nM, about 700 nM, about 800 nM, about 900 nM, about 1 µM, about 5 µM, about 10 µM, about 25 µM, about 50 µM, about 100 µM, or about 1 mM. In some embodiments, the initial amount of a spike-in that is added to the sample is measured by the number of molecules (e.g., about 1, about 10, about 100, about 1000, about 10,000 ($10^4$), about $10^5$, about $10^6$, about $10^7$, about $10^8$, about $10^9$, or about $10^{10}$ molecules). In some embodiments, a subsequent measurement of the amount of the synthetic nucleic spike-in is determined by measuring the molecular count of the spike-in in the extracted nucleic acid sample.

In some embodiments, the method comprises adding to the sample an initial amount of multiple spike-ins from multiple species in the mixture (e.g., 2, 3, 4, 5, 6, 7, 8, 9, 10, 15, 20, 25, 30, 40, 50 or more spike-ins from different species). In some embodiments, the method comprises adding to the sample multiple species of spike-ins from the same class or category as described herein (e.g., multiple species of bacteria, multiple species of viruses, multiple species of fungi, multiple species of nematodes, multiple species of parasites, multiple species of pests, or multiple species of synthetic nucleic acid molecules). In some embodiments, the method comprises adding to the sample multiple species of spike-ins from two or more classes or categories as described herein (e.g., spike-ins from two, three, or more of the class or category of bacteria, viruses, fungi, nematodes, parasites, and pests). In some embodiments, the method comprises adding to the sample multiple species (e.g., 2, 3, 4, 5, 6, 7, 8, 9, 10, 15, 20, 25, 30, 40, 50 or more species) of bacterial spike-ins, multiple species (e.g., 2, 3, 4, 5, 6, 7, 8, 9, 10, 15, 20, 25, 30, 40, 50 or more species) of viral spike-ins, and multiple species (e.g., 2, 3, 4, 5, 6, 7, 8, 9, 10, 15, 20, 25, 30, 40, 50 or more species) of fungal spike-ins. In some embodiments, the method comprises adding 1, 2, 3, 4, 5, 6, 7, 8, 9, 10, 15, 20, 25, 30, 40, 50 or more spike-ins that are synthetic nucleic acids and adding 2, 3, 4, 5, 6, 7, 8, 9, 10, 15, 20, 25, 30, 40, 50 or more spike-ins that are cells or organisms (e.g., bacteria species, viral species, fungal species, nematode species, parasite species, and/or pest species).

In some embodiments, the step of adding one or more spike-ins comprises adding a dilution series of a known species. For example, in some embodiments, a set of 2, 3, 4, 5, 6, 7, 8, 9, 10 or more spike-ins is added to the sample in which the set comprises a dilution series of a the particular molecule, cell, or organism (e.g., a live or inactivated bacterial species, phytoplasma species, viral species, viroid species, *rickettsia* species, fungal species, helminth species, protozoan, parasite species, and/or pest species). In some embodiments, the concentration of the particular molecule, cell, or organism is reduced by about 5-fold or about 10-fold at each dilution.

Nucleic Acid Extraction

Nucleic acids can be extracted from the sample using methods known in the art. In some embodiments, nucleic acid extraction is accomplished by chemical, physical/mechanical, or enzymatic means or a combination thereof.

In some embodiments, the method comprises extracting nucleic acids from the sample by chemical means. For example, in some embodiments, cell lysis reagents (e.g., detergents such as sodium dodecyl sulfate or chaotrophic salts such as guanidium thiocyanate) are added to the sample to lyse cells. Optionally a protease (including but not limited to proteinase K) can be used.

In some embodiments, the method comprises the use of enzymatic means. For example, in some embodiments, a sample is contacted with an enzyme such as lysozyme that breaks down components of the sample such as cell walls.

In some embodiments, the method comprises the use of physical, mechanical, or other means. For example, in some embodiments, a sample is physically sheared (e.g., by sonication), microwave treated, or thermally shocked.

Nucleic acids can be isolated from the mixture as is known in the art. In some embodiments, phenol/chloroform extractions are used to separate nucleic acids from proteins and lipids in the sample, and the nucleic acids are subsequently precipitated (e.g., by ethanol, isopropanol, or potassium acetate). In some embodiments, the nucleic acids are subjected to a further purification step. For example, in some embodiments, nucleic acids can be purified using a purification column Methods of nucleic acid extraction are described, for example, in Hill et al., *Pathogens,* 2015, 4:335-354; Robe et al., European Journal of Soil Biology, 2003, 39:183-190; and in "Environmental Nucleic Acid Extraction," in ENVIRONMENTAL MICROBIOLOGY, 2005, vol. 397, Leadbetter, J. R., ed, Elsevier Academic Press.

Quantification

In some embodiments, the quantifying step comprises detecting a nucleic acid sequence in the one or more spike-ins. A variety of methods can be used to detect and/or quantify the sequence and amount of the one or more spike-ins that are present in the extracted nucleic acid sample. In some embodiments, detecting the nucleic acid sequence of the one or more spike-ins comprises nucleotide sequencing the one or more spike-ins that are present in the extracted nucleic acid sample. In some embodiments, detecting the nucleic acid sequence of the one or more spike-ins comprises amplifying the one or more spike-ins that are present in the extracted nucleic acid sample. In some embodiments, the quantifying step comprises detecting a detectable tag, label, barcode, or nucleic acid sequence of the spike-in.

Detection methods, including various sequencing and amplification methods, are described in Section V below. Methods of quantifying nucleic acid sequences following extraction and determining extraction efficiencies for the detected sequences are also described, for example, in Devonshire et al., *Anal Bioanal Chem,* 2014, 406:6499-6512.

Once the amount of the one or more spike-ins in the extracted nucleic acid sample is quantified (such as by nucleotide sequencing or amplification), the quantified amount of the one or more spike-ins in the extracted nucleic acid sample is compared to the initial amount of the one or more spike-ins that was added to the sample in order to quantify the efficiency of the nucleic acid extraction. In some embodiments, a quantified amount of a spike-in that is less than 90%, less than 85%, less than 80%, less than 75%, less than 70%, less than 60%, less than 50%, or lower, of the initial amount of the spike-in that was added to the sample, is indicative of inefficiency in nucleic acid extraction. In some embodiments, the method comprises correlating a property or characteristic of the spike-in for which the quantified amount is less than 80% of the initial amount with a property or characteristic of the sample that is affecting the efficiency of nucleic acid extraction. As a non-limiting example, if a spike-in has a particular pH (e.g., a basic pH) and the quantified amount of the spike-in is less than 90% of the initial amount of the spike-in, the inefficiency of nucleic acid extraction can be correlated with the pH of the sample. In some embodiments, the method comprises the use of multiple spike-ins that exhibit a range of a particular property. For example, in some embodiments, multiple spike-ins can be used that exhibit a range of pHs. The use of multiple spike-ins can be advantageous, for example, for determining the nucleic acid extraction conditions that result in optimal nucleic acid extraction efficiency for a particular property of interest (e.g., pH) or for determining the nucleic acid extraction conditions that result in the least inefficiencies over a range of properties (e.g., over a range of pHs).

V. Methods of Quantifying Target Capture, Enrichment, and/or Amplification

In another aspect, methods for quantifying multiple targets in a population of nucleic acid sequences are provided. In some embodiments, the method comprises:
(a) providing a sample comprising a population of extracted nucleic acid sequences and further comprising an initial known amount of a plurality of spike-ins, wherein the nucleic acid sequences are extracted from a sample comprising multiple species;
(b) detecting the sequence and amount of (i) a plurality of species targets from the population of extracted nucleic acid sequences and (ii) the spike-ins that are present in the sample; and
(c) normalizing the detected amounts of the detected plurality of species targets from step (b) based on the ratio of the initial amounts of the spike-ins and the detected amounts of the spike-ins, thereby quantifying multiple targets in a population of nucleic acid sequences.

In some embodiments, the starting sample (e.g., an environmental sample) is a sample as described in Section III above. In some embodiments, the sample comprises a mixture of multiple species, e.g., such as one or more bacterial species, phytoplasma species, viral species, viroid species, *rickettsia* species, fungal species, helminth species, protozoan, parasite species, and/or pest species. In some embodiments, the sample comprises one or more bacterial species, phytoplasma species, viral species, viroid species, *rickettsia* species, fungal species, helminth species, protozoan, parasite species, and/or pest species that are plant pathogens. In some embodiments, the targets that are quantified are pathogens (e.g., pathogens that are bacterial species, phytoplasma species, viral species, viroid species, *rickettsia* species, fungal species, helminth species, protozoan, parasite species, and/or pest species). In some embodiments, the targets that are quantified are plant pathogens.

In some embodiments, the sample of step (a) is a sample that has been subjected to a nucleic acid extraction step. Methods of extracting nucleic acid from a sample are described in Section IV above. In some embodiments, the initial amount of the plurality of spike-ins are added to the sample comprising a population of extracted nucleic acid sequences after the nucleic acid sequences are extracted from the sample comprising multiple species. In some embodiments, the initial amount of the plurality of spike-ins are added to the sample comprising multiple species prior to extracting the nucleic acid sequences.

In some embodiments, a random barcode is added to the extracted nucleic acid sequence. Methods of labeling polynucleotide sequences with barcodes or UMIs are described in Section II above. See also, Kivioja et al., *Nature Methods*, 2012, 9:72-76.

Spike-Ins

In some embodiments, the spike-in is a cell or organism as discussed in Section II above (e.g., a live (e.g., attenuated) or inactivated species of a cell or organism, or a mutated cell or organism that is a bacterial species, phytoplasma species, viral species, viroid species, *rickettsia* species, fungal species, helminth species, protozoan, parasite species, or pest species). In some embodiments, the spike-in is a synthetic nucleic acid (e.g., synthetic DNA or RNA sequence) as discussed in Section II above.

In some embodiments, a spike-in is a synthetic nucleic acid sequence that comprises a sequence corresponding to a species target sequence. As used herein, the term "corresponding to a species target sequence" means that the synthetic nucleic acid spike-in comprises a sequence that is identical to a sequence in the species target (e.g., a sequence in the species target to be detected). In some embodiments, a sequence in a synthetic nucleic acid spike-in that corresponds to a species target sequence is at least about 10, 20, 30, 40, 50, 60, 70, 80, 90, 100, 150, 200, 250, 300, 350 bases or more in length.

In some embodiments, the plurality of spike-ins comprises a concentration ladder of spike-ins for evaluating differential amplification of multiple species targets based on concentration. For example, in some embodiments, a set of spike-ins comprising 2, 3, 4, 5, 6, 7, 8, 9, 10 or more different concentrations of a particular cell or organism or synthetic nucleic acid sequence is added to the sample. In some embodiments, a plurality of sets of spike-ins comprising a concentration ladder are added to the sample (e.g., 2, 3, 4, 5, 6, 7, 8, 9, 10, 11, 12, 13, 14, 15, 16, 17, 18, 19, 20 or more sets of concentration ladders).

In some embodiments, the spike-ins comprise a set of synthetic nucleic acid composition ladders of varying nucleotide content, wherein the nucleic acid sequences of the spike-ins comprise a variable sequence region of varying adenine, thymine, cytosine, and/or guanine content flanked by a forward primer binding sequence and a reverse primer binding sequence. As discussed in Section II above, in some embodiments, a synthetic nucleic acid spike-in can comprise a variable sequence region of varying adenine, thymine, cytosine, and/or guanine content (e.g., at least 50%, at least 55%, at least 60%, at least 65%, at least 70%, at least 75%, at least 80%, at least 85%, at least 90%, at least 95%, or more of the variable sequence region is one of adenine, thymine, cytosine, or guanine) flanked by a forward primer binding sequence and a reverse primer binding sequence. In some embodiments, the spike-ins comprise a set of synthetic nucleic acid composition ladders of varying cytosine and guanine content. Nucleic acid composition ladders can be advantageous, for example, for evaluating biases in the efficiency of nucleic acid capture, enrichment, or amplification based on nucleotide content of the sample. An exemplary set of nucleic acid composition ladders is depicted in Table 1 below. In Table 1, a detected amount of 4 copies has been arbitrarily assigned a deduced normalization ratio of 1.0.

TABLE 1

Nucleic acid composition ladder

| Intervening spike in sequence (targeted by the same flanking set of primers) | Actual amount of spike in (molarity) | Detected amount of spike in (number of sequence reads) | Deduced normalization ratio |
|---|---|---|---|
| AAAAAAAA | 1.0 uM | 2 copies | 2.0 |
| TTTTTTTT | 1.0 uM | 4 copies | 1.0 |
| GGGGGG | 1.0 uM | 2 copies | 2.0 |
| CCCCCC | 1.0 uM | 0 copies | 4.0 |
| ATATATAT | 1.0 uM | 4 copies | 1.0 |
| GCGCGCGC | 1.0 uM | 8 copies | 0.5 |
| ATCATCATC | 1.0 uM | 7 copies | 0.57 |
| ATGATGATG | 1.0 uM | 8 copies | 0.5 |

Enrichment and Detection

In some embodiments, prior to detecting the plurality of species targets and the plurality of spike-ins that are present in the sample, the method further comprises enriching the sample for a subset of species targets from the population of extracted nucleic acid sequences. In some embodiments, the step of enriching the sample for a subset of species targets comprises adding a plurality of sets of capture primers to the sample of step (a), wherein each set of capture primers comprises a forward capture primer and a reverse capture primer targeting a nucleic acid sequence in a species. In some embodiments, subsequent to the step of enriching the sample for a subset of species targets, the method further comprises amplifying a plurality of species targets in the enriched sample.

In some embodiments, the enriching step comprises enriching the sample for one class or category of species as described herein (e.g., enriching the sample for bacteria or for a subset of bacterial species, enriching the sample for phytoplasma or for a subset of phytoplasma species, enriching the sample for viruses or for a subset of viral species, enriching the sample for viroids or a subset of viroid species, enriching the sample for fungi or for a subset of fungal species, enriching the sample for helminths or for a subset of helminth species, enriching the sample for protozoans or for a subset of protozoan species, enriching the sample for parasites or for a subset of parasite species, or enriching the sample for pests or for a subset of pest species). In some embodiments, the enriching step comprises enriching the sample for two, three, or four classes or categories of species as described herein (e.g., enriching a sample for two, three, or four of bacteria, phytoplasma, viruses, viroids, *rickettsia*, fungi, helminths, protozoans, parasites, and pests, e.g., enriching a sample for bacterial, fungal, and viral species or subsets of bacterial, fungal, and viral species).

Any of a number of methods can be used for enriching a sample. As non-limiting examples, in some embodiments, the enriching step comprises hybridization selection, in which a capture probe or probes bind to a target genome; subtractive hybridization, in which a capture probe or probes bind to background genome; post-amplification hybrid selection, in which a capture probe or probes bind to target fragments after the construction of a sequencing library; or size selection, in which a target or targets of interest have a characteristic size that enables enrichment through size purification.

In some embodiments, the step of enriching a sample comprises bead or array-based enrichment. For example, in some embodiments, capture probes are attached to beads or to arrays and then are contacted with a sample (e.g., an extracted nucleic acid sample). The species (e.g., nucleic acid sequences in the extracted nucleic acid sample) that bind to the capture probes are retained for a subsequent detection step (e.g., a subsequent sequencing reaction).

In some embodiments, prior to detecting the plurality of species targets and the plurality of spike-ins that are present in the sample, the method further comprises a "de-enrichment" step in which unwanted species are captured and in which the species to be detected are part of an uncaptured pool. For example, in some embodiments, capture probes are attached to beads or to arrays and then are contacted with a sample (e.g., an extracted nucleic acid sample). The species (e.g., nucleic acid sequences in the extracted nucleic acid sample) that do not bind to the capture probes are retained for a subsequent detection step (e.g., a subsequent sequencing reaction).

In some embodiments, the method comprises enriching for and/or detecting a combination of one or more conserved regions of each species target and one or more divergent or highly evolving regions of each species target. For example, in some embodiments a sample is enriched for a subset of species (e.g., a subset of bacterial species, phytoplasma species, viral species, viroid species, *rickettsia* species, fungal species, helminth species, protozoan species, parasite species, and/or pest species) using capture primers that target one or more conserved regions, and detection is carried out on the enriched sample by detecting conserved regions, highly evolved regions, or a combination thereof, thereby identifying one or more target species at the species level, as well as at the sub-species level and/or strain level.

In some embodiments, the method comprises enriching for and/or detecting the amount and sequence of multiple bacterial targets by enriching for and/or detecting a combination of one or more conserved bacterial regions and one or more highly evolving bacterial regions. For example, in some embodiments, bacterial targets can be enriched and/or detected by targeting one or more 16S rRNA sequences. 16S rRNA is known to be a common housekeeping sequence in bacteria that has both highly conserved and variable regions. See, e.g., Isenbarger et al., *Orig Life Evol Biosph*, 2008, DOI: 10.1007/s11084-008-9148-z. In some embodiments, a method of enriching for and/or detecting bacterial targets comprises enriching for and/or detecting one or more 16S rRNA sequences in combination with one or more other gene sequences in bacteria (e.g., one or more housekeeping genes or pathogenicity genes). For example, in some embodiments, a combination of 16S rRNA and one or more sequences selected from pat1, atpD, dnaK, gyrB, ppK, recA, rpoB, HSP1, HSP4, hrpZ, cfl, gap1, rpoD, pgi, kup, acnB, gltA, hrpF, fusA, gapA, lacF, lepA, ppsA, adk, gdhA, hrpB, fliC, egl, gmc, ugpB, pilT, trpB, phaC, mutL, rpoB, and trpB can be targeted for identifying a bacterial species target at the species and sub-species or strain level.

In some embodiments, the method comprises enriching for and/or detecting the amount and sequence of multiple fungal targets by enriching for and/or detecting a combination of one or more conserved fungal regions and one or more highly evolving fungal regions. For example, in some embodiments, fungal targets can be enriched and/or detected by targeting one or more fungal internal transcribed spacer (ITS) rDNA sequences. The ITS regions are non-coding sequences interspersed among highly conserved fungal rDNA and have been shown to have high level of heterogeneity among different fungal genera and species. See, e.g., Iwen et al., Med. Mycol., 2002, 40:87-109. In some embodiments, a method of enriching for and/or detecting fungal targets comprises targeting one or more ITS (e.g., ITS1, ITS2, ITS3, ITS4, ITS5, and/or ITS6) rDNA sequences in combination with one or more other gene sequences selected from TEF1, RPB1, RPB2, calmodulin (CaM), β-tubulin (benA), histone H3 (HIS), nuclear ribosomal intergenic spacer region (IGS rDNA), internal transcribed spacer region (ITS rDNA), nuclear ribosomal RNA large subunit (28S or LSU rDNA) and mitochondrial small subunit (mtSSU rDNA) in fungi.

In some embodiments, the method comprises enriching for and/or detecting the amount and sequence of multiple viral targets by enriching for and/or detecting a combination of one or more conserved viral regions and one or more highly evolving viral regions. For example, in some embodiments, viral targets can be enriched and/or detected by targeting one or more RdRP (RNA-dependent RNA polymerase) sequences. RdRPs are highly conserved among viruses. See, e.g., Bruenn, *Nucleic Acids Res*, 2003, 31:1821-1829. In some embodiments, a method of enriching for and/or detecting viral targets comprises targeting one or more RdRP sequences in combination with one or more other gene sequences in viruses, such as structural genes (e.g., genes encoding a capsid, envelope, or membrane component), non-structural genes (e.g., genes encoding a polymerase, protease, or integrase), polyprotein genes, non-translated regions, regulators of viral and host gene expression, or genes of unknown function.

In some embodiments, the method comprises enriching for and/or detecting the amount and sequence of multiple helminth (e.g., nematode) targets by enriching for and/or detecting a combination of one or more conserved helminth (e.g., nematode) regions and one or more highly evolving helminth (e.g., nematode) regions. For example, in some embodiments, nematode targets can be enriched and/or detected by targeting one or more 18S rRNA sequences. 18S rRNA is known to be a common housekeeping sequence in helminths such as nematodes. See, e.g., Floyd et al., *Molecular Ecology Notes*, 2005, 5:611-612; Hadziavdic et al., *PLoS One*, 2014, 9(2):e87624. In some embodiments, a method of enriching for and/or detecting helminth targets comprises targeting one or more 18S rRNA sequences in combination with one or more other gene sequences in helminths, such as 18S, 28S, ITS, CO1, COX1, or other mitochondrial genes.

In some embodiments, a method of enriching for and/or detecting one or more classes or categories of species as described herein, or subsets of one or more classes or categories of species as described herein, comprises the use of Multi-Locus Sequence Typing (MLST). MLST is a nucleotide sequence-based approach for characterizing isolates of bacteria and other organisms by examining the nucleotide sequences of multiple loci encoding housekeeping genes or fragments thereof. See, Maiden, *Annu. Rev. Microbiol.* 2006, 60:561-588. MLST data for various bacterial species and other organisms are available at pubmlst.org/databases.

In some embodiments, a method of enriching for and/or detecting multiple species targets comprises enriching for and/or detecting species targets from two or more categories or classes as described herein (e.g., from two or more of bacteria, fungi, viruses, nematodes, parasites, and pests). In some embodiments, the method of enriching for and/or detecting multiple species targets comprises enriching for and/or detecting 2, 3, 4, 5, 6, 7, 8, 9, 10, 15, 20, 25, 30, 40, 50, 100 or more species.

For detecting and/or quantifying the sequence and amount of the species targets and spike-ins that are present in the sample, any of a variety of methods can be used. In some embodiments, the step of detecting the plurality of spike-ins comprises detecting and/or quantifying a detectable tag, label, barcode, or nucleotide sequence of the spike-in (as described in Section II above). In some embodiments, the detecting step comprises nucleotide sequencing the species targets and spike-ins that are present in the sample. In some embodiments, the detecting step comprises amplifying a plurality of species targets from the population of extracted nucleic acid sequences (and optionally amplifying spike-ins).

Sequencing Methods

In some embodiments, the detecting step comprises nucleotide sequencing the species targets and spike-ins that are present in the sample. Non-limiting examples of nucleotide sequencing include Sanger sequencing, capillary array sequencing, thermal cycle sequencing (Sears et al., *Biotechniques* 13:626-633 (1992)), solid-phase sequencing (Zimmerman et al., *Methods Mol. Cell Biol.* 3:39-42 (1992)), sequencing with mass spectrometry such as matrix-assisted laser desorption/ionization time-of-flight mass spectrometry (MALDI-TOF/MS; Fu et al., *Nature Biotech.* 16:381-384 (1998)), and sequencing by hybridization (Chee et al., *Science* 274:610-614 (1996); Drmanac et al., *Science* 260:1649-1652 (1993); Drmanac et al., *Nature Biotech.* 16:54-58 (1998)). In some embodiments, "next generation sequencing" methods can be used, for example but not limited to, sequencing by synthesis (e.g., HiSeq™, MiSeq™, or Genome Analyzer, each available from Illumina), sequencing by ligation (e.g., SOLiD™, Life Technologies), ion semiconductor sequencing (e.g., Ion Torrent™, Life Technologies), and pyrosequencing (e.g., 454™ sequencing, Roche Diagnostics). In some embodiments, nucleotide sequencing comprises high-throughput sequencing. In high-throughput sequencing, parallel sequencing reactions using multiple templates and multiple primers allows rapid sequencing of genomes or large portions of genomes. See, e.g., WO 03/004690, WO 03/054142, WO 2004/069849, WO 2004/070005, WO 2004/070007, WO 2005/003375, WO 2000/006770, WO 2000/027521, WO 2000/058507, WO 2001/023610, WO 2001/057248, WO 2001/057249, WO 2002/061127, WO 2003/016565, WO 2003/048387, WO 2004/018497, WO 2004/018493, WO 2004/050915, WO 2004/076692, WO 2005/021786, WO 2005/047301, WO 2005/065814, WO 2005/068656, WO 2005/068089, WO 2005/078130, Seo, et al., *Proc. Natl. Acad. Sci. USA* (2004) 101:5488-5493; and Liu et al., *J. BiomedBiotechnol,* 2012, 2012:251364.

In some embodiments, nucleotide sequencing comprises sequencing by synthesis. In sequencing by synthesis, a fluorescently labeled reversible terminator is imaged as each dNTP is added, and then cleaved to allow incorporation of the next base. The sequencing process produces a set of nucleic acid sequence reads of uniform length. The sequencing reaction can be conducted simultaneously on thousands or millions or different template molecules on a solid surface. Methods of sequencing by synthesis are known in the art. See, e.g., Bronner et al., *Curr Protoc Hum Genet,* 2009 July; doi:10.1002/0471142905.hg10802s62; Rohland et al., *Genome Research,* 2012, 22:939-946. One method of sequencing by synthesis utilizes "bridge amplification" to enable the detection of the fluorescent labels. Briefly, a nucleic acid sample is prepared by fragmenting the nucleic acid into fragments of about 200 bases in length and adding adapters to each end. The library of fragments is flowed across a solid surface (flowcell) and the template fragments bind to the surface. A solid phase bridge amplification PCR process, in which individual templates in the library bend and bridge to another complementary oligonucleotide on the flowcell surface in repeated denaturation and extension cycles, creates approximately one million copies of each template in physical clusters on the flowcell surface.

In some embodiments, nucleotide sequencing comprises single-molecule, real-time (SMRT) sequencing. SMRT sequencing is a process by which single DNA polymerase molecules are observed in real time while they catalyze the incorporation of fluorescently labeled nucleotides complementary to a template nucleic acid strand. Methods of SMRT sequencing are known in the art and were initially described by Flusberg et al., *Nature Methods,* 7:461-465 (2010), which is incorporated herein by reference for all purposes. Briefly, in SMRT sequencing, incorporation of a nucleotide is detected as a pulse of fluorescence whose color identifies that nucleotide. The pulse ends when the fluorophore, which is linked to the nucleotide's terminal phosphate, is cleaved by the polymerase before the polymerase translocates to the next base in the DNA template. Fluorescence pulses are characterized by emission spectra as well as by the duration of the pulse ("pulse width") and the interval between successive pulses ("interpulse duration" or "IPD"). Pulse width is a function of all kinetic steps after nucleotide binding and up to fluorophore release, and IPD is a function of the kinetics of nucleotide binding and polymerase translocation. Thus, DNA polymerase kinetics can be monitored by measuring the fluorescence pulses in SMRT sequencing.

In addition to measuring differences in fluorescence pulse characteristics for each fluorescently-labeled nucleotide (i.e., adenine, guanine, thymine, and cytosine), differences can also be measured for non-methylated versus methylated bases. For example, the presence of a methylated base alters the IPD of the methylated base as compared to its non-methylated counterpart (e.g., methylated adenosine as compared to non-methylated adenosine). Additionally, the presence of a methylated base alters the pulse width of the methylated base as compared to its non-methylated counterpart (e.g., methylated cytosine as compared to non-methylated cytosine) and furthermore, different modifications have different pulse widths (e.g., 5-hydroxymethylcytosine has a more pronounced excursion than 5-methylcytosine). Thus, each type of non-modified base and modified base has a unique signature based on its combination of IPD and pulse width in a given context. The sensitivity of SMRT sequencing can be further enhanced by optimizing solution conditions, polymerase mutations and algorithmic approaches that take advantage of the nucleotides' kinetic signatures, and deconvolution techniques to help resolve neighboring methylcytosine bases.

In some embodiments, nucleotide sequencing comprises nanopore sequencing. Nanopore sequencing is a process by which a polynucleotide or nucleic acid fragment is passed through a pore (such as a protein pore) under an applied potential while recording modulations of the ionic current passing through the pore. Methods of nanopore sequencing are known in the art; see, e.g., Clarke et al., *Nature Nanotechnology* 4:265-270 (2009), which is incorporated herein by reference for all purposes. Briefly, in nanopore sequencing, as a single-stranded DNA molecule passes through a protein pore, each base is registered, in sequence, by a characteristic decrease in current amplitude which results from the extent to which each base blocks the pore. An individual nucleobase can be identified on a static strand, and by sufficiently slowing the rate of speed of the DNA translocation (e.g., through the use of enzymes) or improving the rate of DNA capture by the pore (e.g., by mutating key residues within the protein pore), an individual nucleobase can also be identified while moving.

In some embodiments, nanopore sequencing comprises the use of an exonuclease to liberate individual nucleotides from a strand of DNA, wherein the bases are identified in order of release, and the use of an adaptor molecule that is covalently attached to the pore in order to permit continuous base detection as the DNA molecule moves through the pore. As the nucleotide passes through the pore, it is characterized by a signature residual current and a signature dwell time within the adapter, making it possible to discriminate between non-methylated nucleotides. Additionally, different dwell times are seen between methylated nucleotides and the corresponding non-methylated nucleotides (e.g., 5-methyl-dCMP has a longer dwell time than dCMP), thus making it possible to simultaneously determine nucleotide sequence and whether sequenced nucleotides are modified. The sensitivity of nanopore sequencing can be further enhanced by optimizing salt concentrations, adjusting the applied potential, pH, and temperature, or mutating the exonuclease to vary its rate of processivity.

In some embodiments, the method of detecting the sequence and amount of the species targets and spike-ins comprises deep sequencing. Deep sequencing refers to sequencing nucleic acid sequences (e.g., a region of a genome) multiple times, even as many as hundreds or thousands of times. Typically, deep sequencing uses high-throughput sequencing methods to generate a large number of reads (e.g., hundreds to thousands of reads) at a given position. After sequencing, reads are aligned, such as by multiple sequence alignment or by alignment to a reference. Following alignment, the sequence reads are analyzed (e.g., to identify variants from aligned reads). Deep sequencing allows for the detection of rare components in a sample (e.g., cells that occur in a sample at low frequency or rare nucleic acid variants in a population of nucleic acids). In some embodiments, targeted deep sequencing of specific nucleotide sequences (e.g., particular genes of interest) is used to identity rare variants (e.g., variants that occur in less than 1% of a sample population). Methods of deep sequencing are known in the art. See, e.g., Mardis, *Ann. Rev. Genomics Hum. Genet.*, 2008, 9:387-402; McElroy et al., *Microbial Informatics and Experimentation*, 2014, 4:1 (doi: 10.1186/2042-5783-4-1); Schmitt et al., *PNAS*, 2012, 109:14508-14513.

Amplification Methods

In some embodiments, the method further comprises, prior to the detecting step, amplifying a plurality of species targets from the population of extracted nucleic acid sequences. In some embodiments, the amplifying step comprises: adding a plurality of sets of primers to the sample of step (a), wherein each set of primers comprises a forward primer and a reverse primer targeting a nucleotide sequence in the species, and performing an amplification reaction. In some embodiments, the amplification further comprises the use of spike-ins comprising synthetic nucleic acid sequences that correspond to the sets of primers for amplifying the plurality of species targets. In some embodiments, the spike-ins comprise a first primer binding sequence for binding a forward primer and a second primer binding sequence for binding a reverse primer of a primer set.

In some embodiments, the amplification step comprises polymerase chain reaction (PCR), quantitative PCR, or real-time PCR. As discussed below, quantitative amplification (including, but not limited to, real-time PCR) methods allow for determination of the amount of the species targets (and optionally spike-ins) that are present in a sample.

Quantitative amplification methods (e.g., quantitative PCR or quantitative linear amplification) involve amplification of nucleic acid template, directly or indirectly (e.g., determining a Ct value) determining the amount of amplified DNA, and then calculating the amount of initial template based on the number of cycles of the amplification. Amplification of a DNA locus using reactions is well known (see U.S. Pat. Nos. 4,683,195 and 4,683,202; PCR PROTOCOLS: A GUIDE TO METHODS AND APPLICATIONS (Innis et al., eds, 1990)). Typically, PCR is used to amplify DNA templates. However, alternative methods of amplification have been described and can also be employed. Methods of quantitative amplification are disclosed in, e.g., U.S. Pat. Nos. 6,180,349; 6,033,854; and 5,972,602, as well as in, e.g., Gibson et al., *Genome Research* 6:995-1001 (1996); DeGraves, et al., *Biotechniques* 34(1): 106-10, 112-5 (2003); Deiman B, et al., *Mol Biotechnol.* 20(2):163-79 (2002). Amplifications can be monitored in "real time."

In some embodiments, quantitative amplification is based on the monitoring of the signal (e.g., fluorescence of a probe) representing copies of the template in cycles of an amplification (e.g., PCR) reaction. In the initial cycles of the PCR, a very low signal is observed because the quantity of the amplicon formed does not support a measurable signal output from the assay. After the initial cycles, as the amount of formed amplicon increases, the signal intensity increases to a measurable level and reaches a plateau in later cycles when the PCR enters into a non-logarithmic phase. Through a plot of the signal intensity versus the cycle number, the specific cycle at which a measurable signal is obtained from the PCR reaction can be deduced and used to back-calculate the quantity of the target before the start of the PCR. The number of the specific cycles that is determined by this method is typically referred to as the cycle threshold (Ct). Exemplary methods are described in, e.g., Heid et al. *Genome Methods* 6:986-94 (1996) with reference to hydrolysis probes.

One method for detection of amplification products is the 5'-3' exonuclease "hydrolysis" PCR assay (also referred to as the TaqMan™ assay) (U.S. Pat. Nos. 5,210,015 and 5,487, 972; Holland et al., *PNAS USA* 88: 7276-7280 (1991); Lee et al., *Nucleic Acids Res.* 21: 3761-3766 (1993)). This assay detects the accumulation of a specific PCR product by hybridization and cleavage of a doubly labeled fluorogenic probe (the TaqMan™ probe) during the amplification reaction. The fluorogenic probe consists of an oligonucleotide labeled with both a fluorescent reporter dye and a quencher dye. During PCR, this probe is cleaved by the 5'-exonuclease activity of DNA polymerase if, and only if, it hybridizes to the segment being amplified. Cleavage of the probe generates an increase in the fluorescence intensity of the reporter dye.

Another method of detecting amplification products that relies on the use of energy transfer is the "beacon probe" method described by Tyagi and Kramer, *Nature Biotech.* 14:303-309 (1996), which is also the subject of U.S. Pat. Nos. 5,119,801 and 5,312,728. This method employs oligonucleotide hybridization probes that can form hairpin structures. On one end of the hybridization probe (either the 5' or 3' end), there is a donor fluorophore, and on the other end, an acceptor moiety. In the case of the Tyagi and Kramer method, this acceptor moiety is a quencher, that is, the acceptor absorbs energy released by the donor, but then does not itself fluoresce. Thus, when the beacon is in the open conformation, the fluorescence of the donor fluorophore is detectable, whereas when the beacon is in hairpin (closed) conformation, the fluorescence of the donor fluorophore is quenched. When employed in PCR, the molecular beacon probe, which hybridizes to one of the strands of the PCR product, is in the open conformation and fluorescence is detected, while those that remain unhybridized will not fluoresce (Tyagi and Kramer, *Nature Biotechnol.* 14: 303-306 (1996)). As a result, the amount of fluorescence will increase as the amount of PCR product increases, and thus may be used as a measure of the progress of the PCR. Those of skill in the art will recognize that other methods of quantitative amplification are also available.

Another method for detecting amplification products is digital PCR, in which a limiting dilution of the sample is made across a large number of separate PCR reactions so that most of the reactions have no template molecules and give a negative amplification result. Those reactions that are positive at the reaction endpoint are counted as individual template molecules present in the original sample in a 1 to 1 relationship. See, e.g., Kalina et al. *Nucleic Acids Res* 25:1999-2004 (1997) and Vogelstein and Kinzler, PNAS 96:9236-9241 (1999); U.S. Pat. Nos. 6,440,706, 6,753,147, and 7,824,889. Quantitative partitioning is assumed, and the dynamic range is governed by the number of containers available for stochastic separation. The molecules are then detected by PCR and the number of positive containers is counted. Each successful amplification is counted as one molecule, independent of the actual amount of product. In some embodiments, a digital PCR may be a microfluidics-based digital PCR. In some embodiments, a droplet digital PCR may be employed.

Various other techniques for performing quantitative amplification of nucleic acids are also known. For example, some methodologies employ one or more probe oligonucleotides that are structured such that a change in fluorescence is generated when the oligonucleotide(s) is hybridized to a target nucleic acid. For example, one such method involves is a dual fluorophore approach that exploits fluorescence resonance energy transfer (FRET), e.g., LightCycler™ hybridization probes, where two oligo probes anneal to the amplicon. The oligonucleotides are designed to hybridize in a head-to-tail orientation with the fluorophores separated at a distance that is compatible with efficient energy transfer. Other examples of labeled oligonucleotides that are structured to emit a signal when bound to a nucleic acid or incorporated into an extension product include: Scorpions™ probes (e.g., Whitcombe et al., *Nature Biotechnology* 17:804-807, 1999, and U.S. Pat. No. 6,326,145), Sunrise™ (or Amplifluor™) probes (e.g., Nazarenko et al., *Nuc. Acids Res.* 25:2516-2521, 1997, and U.S. Pat. No. 6,117,635), and probes that form a secondary structure that results in reduced signal without a quencher and that emits increased signal when hybridized to a target (e.g., Lux Probes™).

In other embodiments, intercalating agents that produce a signal when intercalated in double stranded DNA may be used. Exemplary agents include SYBR GREEN™, SYBR GOLD™, and EVAGREEN™. Since these agents are not template-specific, it is assumed that the signal is generated based on template-specific amplification. This can be confirmed by monitoring signal as a function of temperature because melting point of template sequences will generally be much higher than, for example, primer-dimers, etc.

Normalization

In some embodiments, the quantified amounts of spike-ins that are detected in the extracted nucleic acid sample are compared to the initial amount of the spike-ins that are present in the sample for normalizing the detected amount of the species targets. For example, in some embodiments, the measurements obtained from the spike-ins are used to correct for biases in nucleic acid extraction, amplification, and/or sequencing, such as biases with regard to concentration of the species targets, nucleic acid composition (e.g., GC content), and differential relative efficiency of capture or amplification between species targets.

In some embodiments, the normalizing step comprises determining the relative efficiency of amplification of a first species target, relative to a second species target in the population of nucleic acid sequences. In some embodiments, a plurality of species targets from the population of extracted nucleic acid sequences are amplified using a plurality of sets of primers, wherein each set of primers comprises a forward primer and a reverse primer targeting a nucleotide sequence in the species. Spike-ins comprising synthetic nucleic acid sequences that correspond to the sets of primers for amplifying the plurality of species targets, wherein the spike-ins comprise a first primer binding sequence for binding a forward primer and a second primer binding sequence for binding a reverse primer of a primer set, are also added to the sample prior to the amplification reaction. After the amplification reaction, the spike-ins are detected and quantitated. By comparing the quantitated amount of a first spike-in, which corresponds to a first species target (i.e., comprises the primer binding sequences for binding the primers that target a nucleotide sequence of the first species target) to the quantitated amount of a second spike-in, which corresponds to a second species target, differences in the efficiency of amplification between the two targets can be determined. See, FIG. 1.

In some embodiments, the normalizing step comprises correcting for biases in nucleic acid composition. In some embodiments, spike-ins are added to the sample which comprise a set of synthetic nucleic acid composition ladders of varying nucleotide content, wherein the nucleic acid sequences of the spike-ins comprise a variable sequence region of varying adenine, thymine, cytosine, and/or guanine content flanked by a forward primer binding sequence and a reverse primer binding sequence. In some embodiments, the spike-in sequences in the set are identical to each other except for the variable sequence region (e.g., the forward primer binding sequence is the same for each of the spike-ins in the set of synthetic nucleic acid composition ladders, and the reverse primer binding sequence is the same for each of the spike-ins in the set of synthetic nucleic acid composition ladders). The spike-ins are added to the sample in an initial known amount. In some embodiments, the initial amount is the same for all of the spike-ins in the set. Following one or more steps such as nucleic acid extraction, capture, enrichment, and/or amplification, the spike-ins from the set of synthetic nucleic acid composition ladders are detected and quantitated. A normalization ratio can be deduced for each spike-in by comparing the initial amount to the detected amount. This normalization ratio can then be used to normalize the data for species targets, thereby correcting for biases based on nucleotide content, such as differential amplification of multiple species targets based on nucleotide content. See, Table 1.

In some embodiments, the normalizing step comprises using quality scores from sequencing reads of the plurality of species targets and spike-ins. A quality score relates to the probability that a base call for each nucleotide of a sequencing read is incorrect. Methods for calculating quality scores for sequencing reads are known in the art.

VI. Primer Pools for Detecting Targets

In still another aspect, methods for detecting a target in a population of nucleic acid sequences using a pool of primers are provided. In another aspect, compositions comprising a pool of primers as described herein are provided. As is described in further detail below, the primer pools introduce variation at one or more nucleotide positions of a primer sequence that binds to a particular target sequence (e.g., a target sequence in a bacterial species, phytoplasma species, viral species, viroid species, *rickettsia* species, fungal species, helminth species, protozoan, parasite species, or pest species).

The use of a complex primer pool comprising variation at one or more nucleotide positions is advantageous, for example, for detecting genomic variation in a population (e.g., mutated targets or targets that are rare variants in a population). In some embodiments, the use of a complex primer pool is advantageous for identifying mutated bacterial species, phytoplasma species, viral species, viroid species, *rickettsia* species, fungal species, helminth species, protozoan, parasite species, and/or pest species in a sample (e.g., for identifying new or rare pathogen variants).

The use of a complex primer pool comprising variation at one or more nucleotide positions is also advantageous for generating primers that optimize secondary structure (e.g., primer dimers) and off-target avoidance. The complex primer pools described herein are also advantageous for identifying primers that work most effectively in amplifying genetic material from a sample such as a pathogen, with or without a mutation in a target sequence. For example, the complex primer pools can be used for a primer composition assay in which the primer pool is used for amplifying nucleic acid sequences in a single amplification (e.g., PCR) cycle, and the amplified products are then sequenced to determine which sequence is the most enriched in the PCR product. By comparing the relative enrichment of the PCR product to the initial amount of the primers in the primer pool, it can be determined which primer is the most efficient at amplifying its target sequence.

In some embodiments, the method of detecting a target comprises:
(a) providing a sample comprising a population of extracted nucleic acid sequences, wherein the nucleic acid sequences are extracted from a sample comprising multiple species;
(b) adding to the sample of step (a) a pool of primers, wherein the pool of primers comprises (i) a plurality of primers that comprise a consensus binding sequence, and (ii) a plurality of primers that comprise a sequence with at least one nucleotide variation from the consensus binding sequence, wherein the pool of primers results in variation at one or more nucleotide positions of the consensus binding sequence such that for the varied nucleotide position, at least two different nucleotides selected from adenine, thymine, cytosine, and guanine are represented in the varied nucleotide position in the pool of primers;
(c) amplifying the sample of step (b); and
(d) detecting the presence of the target.

In some embodiments, the pool of primers results in variation at one or more nucleotide positions of the consensus binding sequence such that for the varied nucleotide position, at least one primer has an adenine nucleotide, at least one primer has a thymine nucleotide, at least one primer has a cytosine nucleotide, and at least one primer has a guanine nucleotide.

In some embodiments, step (b) comprises adding to the sample a plurality of pools of primers (e.g., one pool of primers comprising forward primer sequences, and one pool of primers comprising reverse primer sequences).

Primer Pools

In some embodiments, a pool of primers comprises a plurality of primers, wherein each primer comprises a binding sequence for binding to a wild-type target sequence. In the pool of primers, some but not all of the primers comprise a "consensus binding sequence," which, as used herein, is a sequence that is entirely complementary to the wild-type target sequence. In some embodiments, a consensus binding sequence has a length of about 8 to about 50 nucleotides, a length of about 10 to about 40 nucleotides, a length of about 15 to about 25 nucleotides, a length of about 20 to about 40 nucleotides, or a length of about 20 to about 30 nucleotides, e.g., about 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 nucleotides.

The remaining primers in the pool of primers comprise a sequence with at least one nucleotide variation or "mismatch" from the consensus binding sequence. In some embodiments, the primers comprising a sequence with at least one nucleotide variation from the consensus binding sequence have 1, 2, 3, 4, 5, or 6 variations or mismatches relative to the consensus binding sequence. In some embodiments, the pool of primers comprises primers with different numbers of mismatches (e.g., primers with one variation from the consensus binding sequence and primers with two variations from the consensus binding sequence). In some embodiments, the 3' region of the primers (e.g., the last 3-5 nucleotides at the 3' end) does not comprise a nucleotide variation or mismatch relative to the consensus binding sequence. Thus, in some embodiments, the pool of primers comprises primers having a sequence with at least one nucleotide variation from the consensus binding sequence, wherein the last 3, 4, or 5 nucleotides at the 3' end of the primer do not comprise the at least one nucleotide variation.

In some embodiments, the number of variations or mismatches that can be tolerated by the primers with at least one nucleotide variation from the consensus binding sequence depends on the length of the primer and the number of nucleotides that are present to complement the annealing temperature. For example, in some embodiments, the length of the primer and the number of G/C pairs in the primer sequence will affect the number of variations or mismatches from the consensus binding sequence that can be present in the primers with at least one nucleotide variation.

In some embodiments, the primers with at least one nucleotide variation from the consensus binding sequence have sufficient similarity to the consensus binding sequence that the primers can hybridize to the wild-type target sequence under stringent hybridization conditions. The phrase "stringent hybridization conditions" refers to conditions under which a primer comprising a sequence that is complementary to a nucleic acid target sequence will hybridize preferentially to its target sequence, typically in a complex mixture of nucleic acids, but to a lesser extent to, or not at all to, other sequences. Stringent conditions are sequence-dependent and will be different in different circumstances. In some embodiments, hybridization conditions for a target sequence are determined based on the ratio of the melting temperature to that target as compared to all other genomic loci that are in the same reaction.

The primer pool has a sufficient number of primers comprising a sequence with at least one nucleotide variation from the consensus binding sequence such that for the varied nucleotide position of the consensus binding sequence, at least two different nucleotides (e.g., at least two of adenine, thymine, cytosine, and guanine nucleotides) are present at least once in the primer pool. In some embodiments, for the varied nucleotide position, at least three different nucleotides (e.g., at least three of adenine, thymine, cytosine, and guanine nucleotides) are present at least once in the primer pool. In some embodiments, for the varied nucleotide position, an adenine, thymine, cytosine, and guanine nucleotide is present at least once in the primer pool. As a non-limiting example, if the consensus binding sequence has an adenine at the first nucleotide position, and the primer pool comprises primers having a nucleotide variation at the first nucleotide position, in some embodiments, at least one primer has an alternative nucleotide (i.e., a thymine, cytosine, or guanine) at the first nucleotide position.

In some embodiments, the primer pool results in variation at one or more nucleotide positions of the consensus binding sequence. In some embodiments, the primer pool results in variation at 1, 2, 3, 4, 5, 6, 7, 8, 9, 10 or more nucleotide positions of the consensus binding sequence. In some embodiments, the primer pool results in variation in at least about 25%, at least about 30%, at least about 40%, at least about 50%, at least about 60%, at least about 70%, at least about 75%, at least about 80%, at least about 90%, or at least about 95% of the nucleotide positions of the consensus binding sequence. In some embodiments, the primer pool results in variation at all of the nucleotide positions of the consensus binding sequence.

In some embodiments, the primers in the pool have a length of about 8-50 nucleotides, about 10 to about 40, about 15 to about 30, about 15 to about 25, about 20 to about 50, or about 20 to about 35 nucleotides, e.g., about 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 nucleotides.

In some embodiments, up to about 97% of the primers in the pool have the consensus binding sequence. In some embodiments, at least about 10% up to about 97%, at least about 10% up to about 90%, at least about 10% up to about 70%, at least about 20% up to about 97%, at least about 20% up to about 90%, at least about 20% up to about 70%, at least about 30% up to about 97%, at least about 40% up to about 97%, at least about 50% up to about 97%, at least about 50% up to about 95%, at least 50% up to about 90%, at least about 60% up to about 97%, at least about 60% up to about 95%, at least 60% up to about 90%, at least about 70% up to about 97%, at least 70% up to about 95%, at least 70% up to about 90%, at least about 80% up to about 97%, or at least about 80% up to about 95% of the primers in the pool have the consensus binding sequence. In some embodiments, at least about 3% up to about 90%, at least about 3% up to about 80%, at least about 3% up to about 70%, at least about 3% up to about 60%, at least about 3% up to about 50%, at least about 5% to about 50%, at least about 3% up to about 40%, at least about 5% up to about 40%, at least about 3% to about 30%, at least about 5% to about 30%, at least about 3% to about 20%, at least 5% up to about 20%, at least about 3% to about 15%, at least about 5% to about 15%, at least about 3% to about 10%, or at least about 5% to about 10% of the primers in the pool have a sequence with at least one nucleotide variation from the consensus binding sequence. In some embodiments, the percentage of primers in the pool that have the consensus binding sequence is greater than the percentage of primers that have the same sequence comprising at least one nucleotide variation from the consensus binding sequence.

Figure 3:
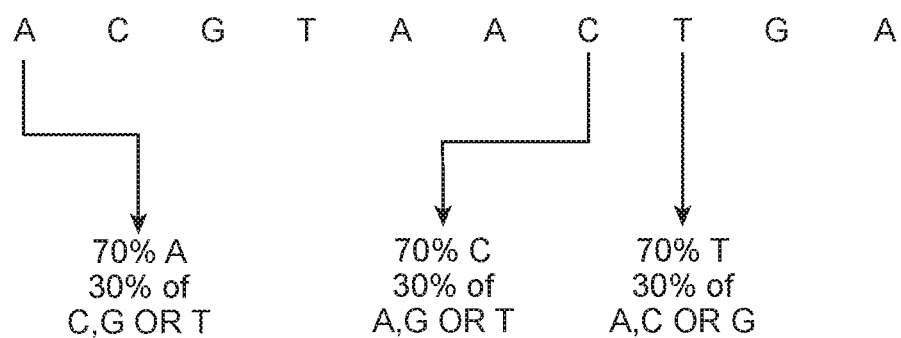
FIG. 3. This figure depicts an example of nucleotide variation from a consensus sequence for generating complex primer pools. For a given nucleotide position, "70% consensus nucleotide incorporation" means that 30% of the nucleotides at the position are non-consensus. For example, in the consensus sequence "ACGTAACTGA" (SEQ ID NO: 1) shown in FIG. 3, 70% consensus nucleotide incorporation at the first nucleotide position means that 70% of the nucleotides in the primer pool at the first nucleotide position are A, while 30% of the nucleotides at the position are non-consensus (C, G, or T). The distribution of the non-consensus nucleotides can be evenly split (10% C, 10% G, and 10% T), or distribution can be skewed.

In some embodiments, in the primer pool, for a particular nucleotide position of the primer consensus binding sequence, at least about 50% up to about 97%, at least about 50% up to about 95%, at least 50% up to about 90%, at least about 60% up to about 97%, at least about 60% up to about 95%, at least 60% up to about 90%, at least about 70% up to about 97%, at least 70% up to about 95%, at least 70% up to about 90%, at least about 80% up to about 97%, or at least about 80% up to about 95% of the nucleotides in the primer pool are the consensus nucleotide. In some embodiments, in the primer pool, for a particular nucleotide position of the primer consensus binding sequence, at least about 3% up to about 50%, at least about 5% to about 50%, at least about 3% up to about 40%, at least about 5% up to about 40%, at least about 3% to about 30%, at least about 5% to about 30%, at least about 3% to about 20%, at least 5% up to about 20%, at least about 3% to about 15%, at least about 5% to about 15%, at least about 3% to about 10%, or at least about 5% to about 10% of the nucleotides in the pool are alternative or non-consensus nucleotides (i.e., a nucleotide other than the consensus nucleotide at that particular nucleotide position). In some embodiments, in the primer pool, for a particular nucleotide position of the primer consensus binding sequence, each of the non-consensus nucleotides makes up at least about 1% up to about 17%, at least about 1% up to about 15%, at least about 1% up to about 10%, at least about 1% up to about 5%, at least about 1% up to about 4%, at least about 1% up to about 3%, at least about 2% up to about 10%, at least about 2% up to about 5%, or at least about 2% up to about 4% (e.g., about 2%, about 2.5%, about 3%, about 3.5%, or about 4%). As used herein, the terms "consensus nucleotide" and "non-consensus nucleotide" refer to a nucleotide (adenine, thymine, cytosine, or guanine nucleotide) that is present at a given position in a primer sequence. A primer having a consensus nucleotide at a given position is a primer that has the same nucleotide as the nucleotide that is present at the corresponding position in the consensus binding sequence. A primer having a non-consensus nucleotide at a given position is a primer that has a different nucleotide as the nucleotide that is present at the corresponding position in the consensus binding sequence. For example, for a consensus sequence "ACGTAACTGA" (SEQ ID NO: 1) a primer has a consensus nucleotide at the position corresponding to the first position of the consensus binding sequence if the primer has an adenine nucleotide at that position; a primer has a non-consensus nucleotide at the position corresponding to the first position of the consensus binding sequence if the primer has a thymine, cytosine, or guanine nucleotide at that position. See, e.g., FIG. 3 and FIG. 4.

In some embodiments, for a particular nucleotide position of the primer consensus binding sequence, one, two, or three different non-consensus or alternative nucleotides (i.e., nucleotides other than the consensus nucleotide at that particular position) are present in the primer pool. In some embodiments, for a particular nucleotide position, two different non-consensus nucleotides are present in the primer pool. In some embodiments, for a particular nucleotide position, all three non-consensus nucleotides are present in the primer pool. In some embodiments, for a particular nucleotide position, the different non-consensus nucleotides are present in the pool in approximately equal amounts. As a non-limiting example, in some embodiments, at a given nucleotide position, about 90% of the nucleotides in the primer pool are the consensus nucleotide, and the three non-consensus nucleotides are present in the primer pool in approximately equal amounts of about 3.3%. As another non-limiting example, in some embodiments, at a given nucleotide position, about 92.5% of the nucleotides in the primer pool are the consensus nucleotide, and the three non-consensus nucleotides are present in approximately equal amounts of about 2.5%. In some embodiments, for a particular nucleotide position of the primer consensus binding sequence, the different non-consensus nucleotides are not represented in the primer pool in approximately equal amounts. As a non-limiting example, in some embodiments, at a given nucleotide position, about 90% of the nucleotides are the consensus nucleotide, one of the non-consensus nucleotides is present in an amount of about 5%, and two of the non-consensus nucleotides are present in amounts of about 2.5%.

Target Detection

In some embodiments, the target to be detected is a nucleic acid sequence of a bacterial species, phytoplasma species, viral species, viroid species, *rickettsia* species, fungal species, helminth species, protozoan, parasite species, or pest species. In some embodiments, the target to be detected is a nucleic acid sequence of a pathogen (e.g., a pathogen that is a bacterial species, phytoplasma species, viral species, viroid species, *rickettsia* species, fungal species, helminth species, protozoan, parasite species, or pest species). In some embodiments, the target to be detected is a plant pathogen. In some embodiments, the target to be detected is a nucleic acid sequence of a mammalian organism (e.g., a human, primate, equine, bovine, ovine, porcine, rodent, feline, or canine organism).

In some embodiments, the sample is a sample as described in Section III above. In some embodiments, the sample is an environmental sample. In some embodiments, the sample is a biological sample (e.g., a tissue, cell, or blood sample). In some embodiments, the sample comprises a mixture of multiple species, e.g., such as one or more bacterial species, phytoplasma species, viral species, viroid species, *rickettsia* species, fungal species, helminth species, protozoan, parasite species, and/or pest species. In some embodiments, the sample comprises one or more bacterial species, phytoplasma species, viral species, viroid species, *rickettsia* species, fungal species, helminth species, protozoan, parasite species, and/or pest species that are plant pathogens.

In some embodiments, the step of detecting the target comprises determining the sequence of a target nucleic acid sequence. In some embodiments, the step of detecting the target comprises quantitating the amount of the target nucleic acid sequence (e.g., using quantitative PCR, real-time PCR, or digital PCR methods). Methods of determining the sequence of a target nucleic acid sequence and quantitating the amount of a target nucleic acid sequence are described in Section V above.

In some embodiments, the target that is detected is a mutated nucleic acid sequence comprising a sequence that has one or more mutations in the primer binding region relative to a wild-type target sequence that is entirely complementary to the primer consensus binding sequence. Thus, in some embodiments, the target that is detected has a nucleic acid sequence that is not entirely complementary to the primer consensus binding sequence. In some embodiments, the target is a mutated nucleic acid sequence that has 1, 2, 3, 4, 5, or 6 mutations, relative to the wild-type target sequence, in the primer binding site. In some embodiments, the target is a mutated nucleic acid sequence that has one or two mutations, relative to the wild-type target sequence, in the primer binding site.

In some embodiments, the method comprises detecting a wild-type target sequence that is entirely complementary to the consensus binding sequence (e.g., nucleotide sequencing and/or quantifying the amount of the wild-type target sequence). In some embodiments, the method comprises detecting (i) a wild-type target sequence that is entirely complementary to the consensus binding sequence, and (ii) a mutated target sequence that is not entirely complementary to the primer consensus binding sequence. In some embodiments, the method further comprises comparing the amount of the mutated target sequence in the sample to the amount of the wild-type target sequence in the sample.

In some embodiments, the detecting step comprises deep sequencing. In some embodiments, the detecting step comprises deep sequencing a target region (e.g., target gene or target genomic region) and determining the relative abundance in the population of a mutation or variant at the target region (e.g., a mutation in or rare variant of a bacterial species, phytoplasma species, viral species, viroid species, *rickettsia* species, fungal species, helminth species, protozoan, parasite species, and/or pest species).

In some embodiments, the amplifying step (c) comprises performing a single cycle of amplification on the sample of step (b), and the detecting step (d) comprises sequencing the amplification products of step (c). In some embodiments, the relative amount of an amplification product of step (c) is compared to the initial amount of the primer in the primer pool that was used to amplify the product, thereby determining the relative efficiency of the primer for amplifying the product.

In some embodiments, the methods of detecting a target comprising the use of a primer pool as described herein can further comprise adding one or more spike-ins as described herein, e.g., a synthetic nucleic acid spike-in or a cell or organism spike-in as described in Section II above. In some embodiments, spike-ins are used with methods comprising the use of primer pools as described herein for improving the accuracy of quantification or for correcting biases in nucleic acid extraction, amplification, and/or sequencing.

VII. Examples

The following examples are offered to illustrate, but not to limit, the claimed invention.

Example 1: Use of Spike-Ins with Nucleic Acid Detection

In this example, multiple nucleic acid samples are provided for sequencing reactions. Spike-ins are added to each nucleic acid sample prior to sequencing the samples. The spike-ins are one or a combination of the following: a concentration ladder (wherein each unique sequence is spiked in at known amounts to produce a concentration ladder), a GC ladder (wherein each unique sequence has a unique GC composition within the sequence), single stranded RNA, single stranded DNA, double stranded RNA, and/or double stranded DNA spike-ins, or a size ladder (wherein each unique sequence has a different length to form a target length ladder). The spike-ins are flanked by the primers that are used for amplifying target nucleic acid sequences in the sample, so as to determine the amplification efficiency of primers for different targets with varying characteristics. Each spike-in is added in at a known concentration; following amplification and sequencing, the relative identified sequence counts from each spike-in is measured and used to determine an amplification bias curve. The set of curves (and linear or nonlinear combinations of these curves) is used to correct the detected quantity of nucleic acid molecules from the same sample. Thus, spike-ins can be used to correct for variability that occurs between molecular biology experiments that involve enrichment, ligation, amplification, or hybridization.

Example 2: Use of Spike-Ins for Quantitating the Amount of a Pathogen in a Sample In this example, spike-ins are used for quantitating the amount of a pathogen (*Verticillium*) in a given soil sample. A set of spike-ins at various concentrations, which can be specifically amplified with primers that target the *Verticillium* genome, are added to the sample. The genomic material in the sample (which contains both the *Verticillium* genome and the spike-in concentration ladder) is amplified with primers that target the *Verticillium* genome, resulting in sequences derived from the *Verticillium* genome as well as reads from the spike-in concentration ladder. A standard curve is drawn for the spike-ins based on the number of reads that map to spike-in sequence versus the spike-in concentration that was added to the sample. The number of reads derived from the *Verticillium* genome is then mapped to the standard curve and the concentration of *Verticillium* in the sample is extrapolated.

Example 3: Use of Complex Primer Pools for Capturing Variant Targets

In this example, a complex primer pool is tested for its ability to capture variant targets. For rapidly evolving pathogens such as bacteria, virus, or fungi, "consensus" sequences may have evolved in the wild to contain many nucleotide variants from what has been previously sequenced. In other cases, only a small proportion of a large population of similar but variable pathogens within the same family may have been sequenced. This is the case, for example, with many families of fungi and bacteria. To capture this diversity and expand the capture potential of the primers, primers are used that contain random variants from the consensus sequence. These primers are still similar enough to the consensus sequence that they can hybridize to and capture at least one sequenced pathogen within the family of interest. However, the primers are variant enough such that different members of the same family of pathogens may be captured using the same pool of variant primers (where each individual primer is specific but the pool as an aggregate contains variant primers).

For example, a complex primer pool can be used to detect a new strain of pathogen (e.g., *Verticillium*) for which the genome cannot be amplified with existing conventional forward-reverse primer pairs due to the presence of multiple mutations in the binding site for the conventional primer pair (thus preventing the primer pair from sufficiently binding to the genome to enable amplification). In this scenario, the use of a complex primer pool containing a primer derivative comprising variations in the binding site that correspond to the mutations in the new strain of *Verticillium* would enable a primer pair to sufficiently bind to the genome to enable amplification.

Example 4: Use of Complex Primer Pools for Determining Efficiency of Primers

In this example, a complex primer pool is used for determining the most efficient forward and reverse primer pair for a pathogen (e.g., a new strain of *Verticillium*). First, two complex primer pools are synthesized: one derived from the *Verticillium* forward primer sequence, and one derived from the *Verticillium* reverse primer sequence. A "primer competition" experiment is set up using these two primer pools to amplify the extracted genome of the new strain of *Verticillium* (or spike-ins that contain genome sequence from the new strain of *Verticillium*). After one amplification cycle (one round of PCR), the PCR product is deep sequenced. The sequence reads are aligned and quantitated to identify which *Verticillium* forward and reverse primer sequences are overrepresented in the sequenced PCR dataset, relative to the estimated abundances of primer sequences in the forward and reverse primer pools. These overrepresented primer sequences would be sequences that have "won" over other primers in the primer competition experiment, i.e., they are the most efficient amplifiers of the new *Verticillium* strain.

Example 5: Design of Synthetic Spike-Ins

Artificial sequence generation: Synthetic sequences were specifically designed to be non-natural, not occurring in nature and orthogonal to all known DNA sequences within publicly available nucleotide databases. Because the synthetic sequences used in the spike-in do not match any known organism, they will not generate any false positive hits when used in combination with naturally occurring DNA samples (in contrast to spike-in controls that naturally occurring sequences themselves, are based on naturally occurring sequences, or are taken from natural organisms). Our Artificially Unique Sequences (AUS) were generated using a computational algorithm that chose sequences that did not contain significant sequence identity to any part of the genome of an existing organism ever sequenced and placed into any public repository. Variables of the "artificial" sequences tested for functionality were length, GC content, secondary structure, ability to clone and replicate in bacterial host without toxicity, ability to amplify by PCR, and ability to sequence with standard techniques.

Incorporation of transposon sequences: Our synthetic spike in sequences were designed such that a subsequence of the spike-in sequence matched identically to a transposon sequence. The insertion of this transposon sequence ensures that the synthetic spike-in would be efficiently and non-randomly captured by commercially available Next Generation Sequencing library preparation kits that rely on the presence of a transposon sequence for shearing and ligating DNA for preparing sequencing libraries. The inclusion of transposon sequences within the synthetic spike-in sequence promotes the success of the spike-in as a normalization control throughout the entire sequencing workflow.

Our design contained multiple transposon sequences regularly spaced between AUS (Artificially Unique Sequences, described above). This design enables us to test multiple sequence designs, such as, (1) the effect of different transposon sequences on synthetic spike-in processing and inclusion in the final sequencing library; (2) the effect of AUS sequence context (for example, nucleotide repeats, A/T/C/G ratios etc.) on synthetic spike-in processing, and in AUS representation in the final NGS library. The metric used to evaluate these designs is the observed frequency of intervening AUS representation in the final NGS library. Higher representation of intervening AUS in the final library suggests that the transposon sequence is more efficient at being recognized and processed during the NGS library preparation process. If the underlying nucleotide design of the synthetic spike-in is being tested, higher AUS representation in the final library indicates that the AUS sequence is less toxic to the library preparation/sequencing process, and is hence a more desirable sequence. The AUS sequence design can also be used to glean broader understanding about how specific ACGT compositions, sequence constructs (dinucleotide, trinucleotide and quatranucleotide frequencies), sequence secondary structures etc. impact sequence representation in NGS sequencing libraries.

Figure 5:
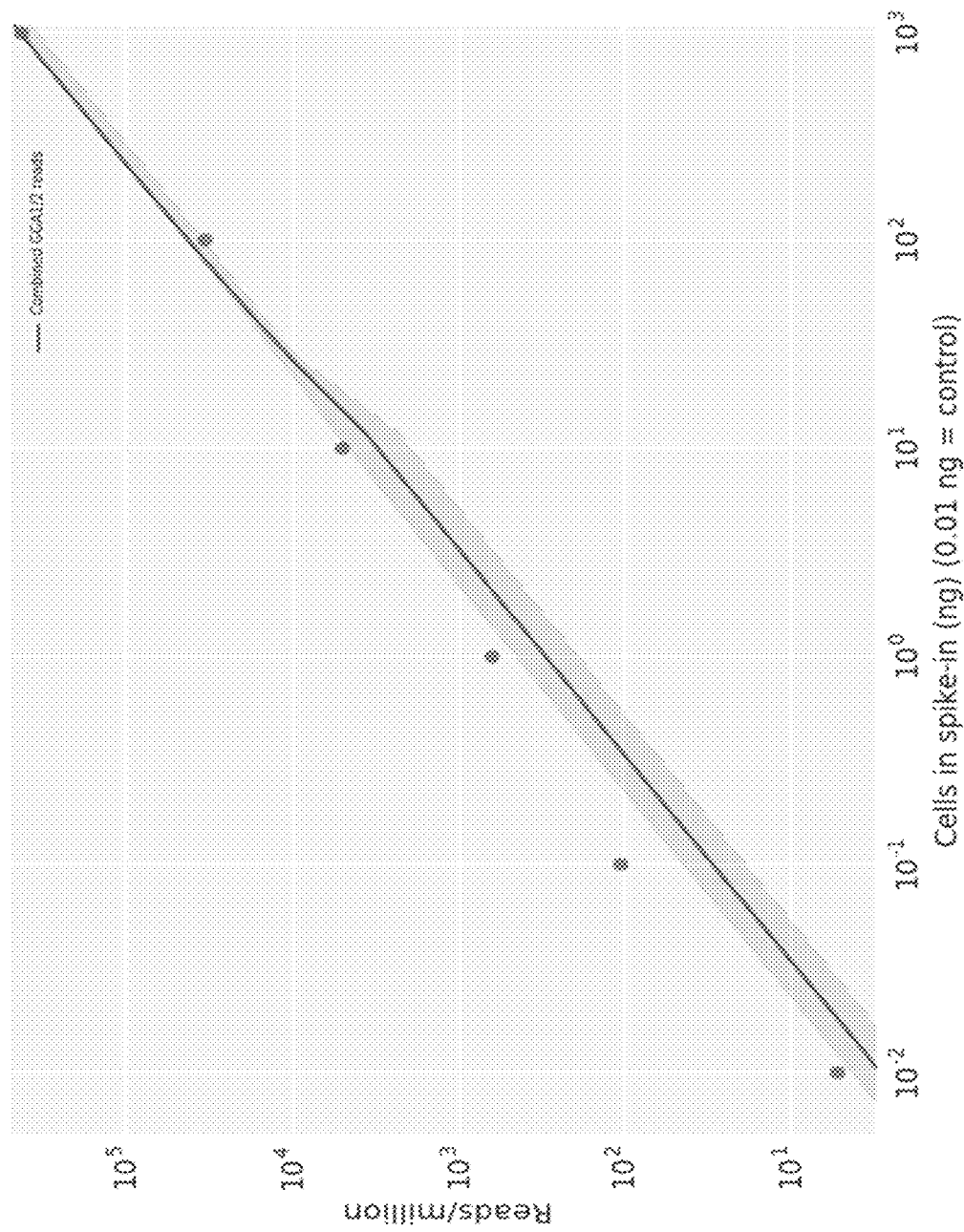
FIG. 5. Sequencing reads obtained as a function of spike-ins added, showing that output is linear with respect to the input amount of DNA (a property desired for normalization controls). Each dot on the graph depicts a sample with varying amounts of added spike-in. The x-axis is the concentration of spike-in added to the sample. The y-axis depicts the number of sequences captured from each sample that match to spike-in for every million reads captured.

Synthetic spike-ins comprising AUS and transposon sequences were spiked into a sample in a dilution series. Libraries were prepared and sequenced from the samples. As shown in FIG. 5, output from the sequencing technique was linear with respect to the input amount of DNA, which is a property that is desired for normalization controls.

Figure 6:
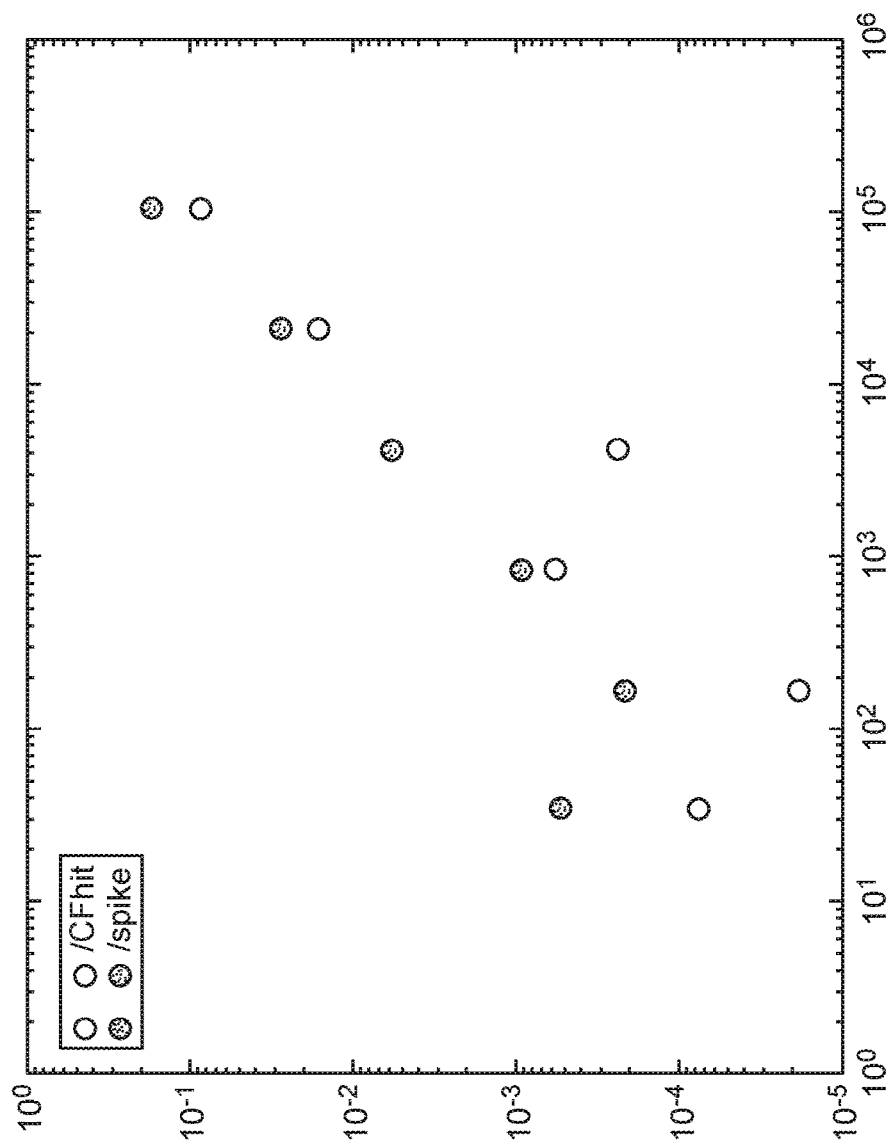

As shown in FIG. 6, the normalization results for quantification of a non-synthetic organism show that spike-in normalization enables linear quantification of non-synthetic organisms.

It is understood that the examples and embodiments described herein are for illustrative purposes only and that various modifications or changes in light thereof will be suggested to persons skilled in the art and are to be included within the spirit and purview of this application and scope of the appended claims. All patents, patent applications, internet sources, database entries, and other published materials cited in this specification are incorporated herein by reference in their entireties. Any discrepancy between any reference material cited herein or any prior art in general and an explicit teaching of this specification is intended to be resolved in favor of the teaching in this specification.

---

What is claimed is:

1. A method for quantifying multiple targets in a population of nucleic acid sequences, the method comprising:
   (a) providing a sample comprising a population of extracted nucleic acid sequences and further comprising an initial known amount of a plurality of spike-ins, wherein the nucleic acid sequences are extracted from a sample comprising multiple species;
   (b) detecting (i) the sequence and amount of a plurality of species targets from the population of extracted nucleic acid sequences and (ii) the amount of the spike-ins that are present in the sample; and
   (c) normalizing the detected amounts of the detected plurality of species targets from step (b) based on the ratio of the initial amounts of the spike-ins and the detected amounts of the spike-ins, thereby quantifying multiple targets in a population of nucleic acid sequences,
   wherein the spike-ins comprise synthetic nucleic acid sequences that comprise an artificial sequence flanked on each end by a transposon sequence.

2. The method of claim 1, wherein the sample comprising multiple species includes one or more bacterial species, phytoplasma species, viral species, viroid species, *rickettsia* species, fungal species, helminth species, protozoan, parasite species, and/or pest species.

3. The method of claim 1, wherein prior to the detecting step, the method further comprises amplifying a plurality of species targets from the population of extracted nucleic acid sequences, wherein the amplifying step comprises:
   adding a plurality of sets of primers to the sample of step (a), wherein each set of primers comprises a forward primer and a reverse primer targeting a nucleotide sequence in the species, and
   performing an amplification reaction.

4. The method of claim 1, wherein prior to the detecting step, the method further comprises enriching the sample for a subset of species targets from the population of extracted nucleic acid sequences, thereby generating an enriched sample.

5. The method of claim 4, wherein subsequent to the step of enriching the sample for a subset of species targets, the method further comprises amplifying a plurality of species targets in the enriched sample.

6. A method for quantifying multiple targets in a population of nucleic acid sequences, the method comprising:
   (a) providing a sample comprising a population of extracted nucleic acid sequences and further comprising an initial known amount of a plurality of spike-ins, wherein the nucleic acid sequences are extracted from a sample comprising multiple species;
   (b) detecting (i) the sequence and amount of a plurality of species targets from the population of extracted nucleic acid sequences and (ii) the amount of the spike-ins that are present in the sample; and (c) normalizing the detected amounts of the detected plurality of species targets from step (b) based on the ratio of the initial amounts of the spike-ins and the detected amounts of the spike-ins, thereby quantifying multiple targets in a population of nucleic acid sequences, wherein the spike-ins comprise a set of synthetic nucleic acid composition ladders of varying nucleotide content, wherein the nucleic acid sequences of the spike-ins comprise a variable sequence region of varying adenine, thymine, cytosine, and/or guanine content flanked by a forward primer binding sequence and a reverse primer binding sequence.

7. The method of claim 6, wherein the normalizing step (c) comprises evaluating the differential amplification of multiple species targets based on nucleotide content by quantifying the amount of each spike-in from the set of synthetic nucleic acid composition ladders and normalizing based on the amount of each spike-in that is detected.

8. The method of claim 6, wherein the sample comprising multiple species includes one or more bacterial species, phytoplasma species, viral species, viroid species, *rickettsia* species, fungal species, helminth species, protozoan, parasite species, and/or pest species.

9. The method of claim 6, wherein prior to the detecting step, the method further comprises amplifying a plurality of species targets from the population of extracted nucleic acid sequences, wherein the amplifying step comprises:

adding a plurality of sets of primers to the sample of step (a), wherein each set of primers comprises a forward primer and a reverse primer targeting a nucleotide sequence in the species, and performing an amplification reaction.

10. The method of claim 6, wherein prior to the detecting step, the method further comprises enriching the sample for a subset of species targets from the population of extracted nucleic acid sequences, thereby generating an enriched sample.

11. The method of claim 10, wherein subsequent to the step of enriching the sample for a subset of species targets, the method further comprises amplifying a plurality of species targets in the enriched sample.

\* \* \* \* \*

SEQUENCE LISTING

<160> NUMBER OF SEQ ID NOS: 7

<210> SEQ ID NO 1
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
acgtaactga                                                          10

<210> SEQ ID NO 2
<211> LENGTH: 10
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2 achtaactga                                                          10

<210> SEQ ID NO 3
<211> LENGTH: 10
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3 acgtabctga                                                          10

<210> SEQ ID NO 4
<211> LENGTH: 10
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 4 acgtaactha                                                              10

<210> SEQ ID NO 5
<211> LENGTH: 10
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5 acgvaadtga                                                              10

<210> SEQ ID NO 6
<211> LENGTH: 10
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6 bcgtbactga                                                              10

<210> SEQ ID NO 7
<211> LENGTH: 10
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7 achtaacvga                                                              10
```